US010544426B2

(12) United States Patent
Hain et al.

(10) Patent No.: US 10,544,426 B2
(45) Date of Patent: Jan. 28, 2020

(54) METHODS OF USING ALS INHIBITOR HERBICIDES FOR CONTROL OF UNWANTED VEGETATION IN ALS INHIBITOR HERBICIDE TOLERANT BETA VULGARIS PLANTS

(75) Inventors: Ruediger Hain, Frankfurt (DE); Gerhard Johann, Burscheid (DE); Guenter Donn, Hofheim (DE)

(73) Assignee: BAYER INTELLECTUAL PROPERTY GMBH, Monheim (DE)

(*) Notice: Subject to any disclaimer, the term of this patent is extended or adjusted under 35 U.S.C. 154(b) by 483 days.

(21) Appl. No.: 13/821,966

(22) PCT Filed: Oct. 13, 2011

(86) PCT No.: PCT/EP2011/067922
§ 371 (c)(1),
(2), (4) Date: Mar. 8, 2013

(87) PCT Pub. No.: WO2012/049266
PCT Pub. Date: Apr. 19, 2012

(65) Prior Publication Data
US 2013/0190179 A1 Jul. 25, 2013

Related U.S. Application Data

(60) Provisional application No. 61/394,469, filed on Oct. 19, 2010.

(30) Foreign Application Priority Data

Oct. 15, 2010 (EP) ..................... 10187759

(51) Int. Cl.
C12N 15/82 (2006.01)
A01N 43/50 (2006.01)
A01N 43/54 (2006.01)
A01N 43/653 (2006.01)
A01N 43/66 (2006.01)
A01N 43/88 (2006.01)
A01N 43/90 (2006.01)

(52) U.S. Cl.
CPC ......... C12N 15/8278 (2013.01); A01N 43/50 (2013.01); A01N 43/54 (2013.01); A01N 43/653 (2013.01); A01N 43/66 (2013.01); A01N 43/88 (2013.01); A01N 43/90 (2013.01); C12N 15/8274 (2013.01)

(58) Field of Classification Search
CPC .... A01N 43/90; A01N 43/50; C12N 15/8274; C12N 15/8278; A01H 4/008
See application file for complete search history.

(56) References Cited

U.S. PATENT DOCUMENTS

| 2,556,664 A | 6/1951 | Smith et al. |
|---|---|---|
| 2,695,225 A | 11/1954 | Witman |
| 2,903,478 A | 9/1959 | Lambrech |
| 2,913,327 A | 11/1959 | Tilles et al. |
| 3,120,434 A | 2/1964 | Pohland |
| 3,175,887 A | 3/1965 | Van den Berg |
| 3,175,897 A | 3/1965 | Tilles et al. |
| 3,177,061 A | 4/1965 | Metivier |
| 3,198,786 A | 8/1965 | Tilles et al. |
| 3,330,821 A | 7/1967 | Harman et al. |
| 3,442,945 A | 5/1969 | Olin |
| 3,480,671 A | 11/1969 | Tilles et al. |
| 3,534,098 A | 10/1970 | Horrom et al. |
| 3,582,314 A | 6/1971 | Konnai et al. |
| 3,692,820 A | 9/1972 | Boroschewski et al. |
| 3,746,532 A | 7/1973 | Kimura et al. |
| 3,836,524 A | 9/1974 | Pitt |
| 3,894,078 A | 7/1975 | Fridinger |
| 4,127,405 A | 11/1978 | Levitt |
| 4,288,244 A | 9/1981 | Kirino et al. |
| 4,385,927 A | 5/1983 | Takematsu et al. |
| 4,394,506 A | 7/1983 | Levitt |
| 4,400,196 A | 8/1983 | Albrecht et al. |
| 4,420,325 A | 12/1983 | Sauers |
| 4,479,821 A | 10/1984 | Meyer et al. |
| 4,593,104 A | 6/1986 | Eicken et al. |
| 4,668,277 A | 5/1987 | Yamamoto et al. |
| 4,746,353 A | 5/1988 | Levitt |
| 4,789,393 A | 12/1988 | Hanagan |
| 4,802,907 A | 2/1989 | Takematsu et al. |
| 4,906,285 A | 3/1990 | Wada et al. |
| 4,932,999 A | 6/1990 | Saito et al. |
| 5,009,699 A | 4/1991 | Brady et al. |
| 5,013,659 A | 5/1991 | Bedbrook et al. |
| 5,090,991 A | 2/1992 | Forster et al. |
| 5,118,339 A | 6/1992 | Tamaru et al. |
| 5,141,870 A | 8/1992 | Bedbrook et al. |

(Continued)

FOREIGN PATENT DOCUMENTS

| CN | 1080116 A | 1/1994 |
|---|---|---|
| DE | 1014380 | 8/1957 |

(Continued)

OTHER PUBLICATIONS

Dexter, Alan G., and Richard K. Zollinger. "Weed control guide for sugarbeet." Sugarbeet Res. Ext. Rep 32 (2001): 3-34.*

(Continued)

Primary Examiner — Weihua Fan
(74) Attorney, Agent, or Firm — McBee Moore & Vanik IP, LLC

(57) ABSTRACT

Present invention relates to the use of the ALS inhibitor herbicides for controlling unwanted vegetation in ALS inhibitor herbicide tolerant *Beta vulgaris* plants, more especially, present invention relates to the use of ALS inhibitor herbicides for control of unwanted vegetation in *Beta vulgaris*, preferably in sugar beet growing areas in which the *Beta vulgaris*, preferably sugar beet comprise a mutation in codon 1705-1707 of an endogenous ALS gene encoding an ALS protein containing an amino acid that is different from tryptophan at position 569, preferably the tryptophan is substituted by leucine.

19 Claims, No Drawings

Specification includes a Sequence Listing.

(56) References Cited

U.S. PATENT DOCUMENTS

| | | | |
|---|---|---|---|
| 5,198,599 A | 3/1993 | Thill | |
| 5,209,771 A | 5/1993 | Meyer | |
| 5,378,824 A * | 1/1995 | Bedbrook | C12N 9/88 435/69.1 |
| 5,457,085 A | 10/1995 | Seckinger et al. | |
| 5,476,936 A | 12/1995 | Philipp et al. | |
| 5,859,348 A * | 1/1999 | Penner | A01H 1/04 435/410 |
| 6,555,375 B1 * | 4/2003 | Golovko | A01H 4/005 435/420 |
| 6,774,085 B1 | 8/2004 | Hacker et al. | |
| 7,422,998 B2 | 9/2008 | Hacker et al. | |
| 7,482,308 B2 | 1/2009 | Araki et al. | |
| 8,008,484 B2 | 8/2011 | Araki et al. | |
| 8,530,386 B2 | 9/2013 | Hacker et al. | |
| 2009/0205064 A1* | 8/2009 | Schopke | C12N 15/8274 800/260 |
| 2009/0215625 A1* | 8/2009 | McElroy | A01N 25/32 504/107 |
| 2010/0248965 A1* | 9/2010 | Hacker | A01N 47/36 504/134 |
| 2010/0285964 A1 | 11/2010 | Waldraff et al. | |
| 2013/0190179 A1 | 7/2013 | Hain et al. | |
| 2013/0247253 A1 | 9/2013 | Hain et al. | |

FOREIGN PATENT DOCUMENTS

| | | | |
|---|---|---|---|
| DE | 1031571 | 6/1958 | |
| DE | 1039779 | 9/1958 | |
| DE | 1567151 | 7/1969 | |
| DE | 1300947 | 8/1969 | |
| DE | 2135768 | 1/1972 | |
| DE | 2305495 | 8/1973 | |
| DE | 2328340 | 12/1973 | |
| DE | 2648008 A1 | 5/1978 | |
| DE | 2822155 A1 | 11/1979 | |
| DE | 3303388 A1 | 8/1983 | |
| DE | 3303388 C2 | 11/1994 | |
| EP | 0007677 B1 | 3/1982 | |
| EP | 0048436 A1 | 3/1982 | |
| EP | 0053011 A1 | 6/1982 | |
| EP | 0048436 B1 | 2/1984 | |
| EP | 0205271 A1 | 12/1986 | |
| EP | 0206251 A1 | 12/1986 | |
| EP | 0084020 B1 | 9/1987 | |
| EP | 0239414 A1 | 9/1987 | |
| EP | 0136061 B1 | 1/1988 | |
| EP | 0120814 B1 | 7/1988 | |
| EP | 0131258 B1 | 8/1989 | |
| EP | 0336151 A2 | 10/1989 | |
| EP | 0348737 A1 | 1/1990 | |
| EP | 0360750 A2 | 3/1990 | |
| EP | 0184385 B1 | 9/1990 | |
| EP | 0447004 A2 | 9/1991 | |
| EP | 0087780 B1 | 10/1991 | |
| EP | 0193259 B1 | 12/1991 | |
| EP | 0476555 A2 | 3/1992 | |
| EP | 0142924 B1 | 4/1992 | |
| EP | 0131624 B1 | 9/1992 | |
| EP | 0221044 B1 | 9/1992 | |
| EP | 0336151 B1 | 3/1993 | |
| EP | 0305939 B1 | 11/1994 | |
| EP | 0502014 B1 | 2/1995 | |
| EP | 0315889 B1 | 7/1996 | |
| EP | 0476555 B1 | 12/1998 | |
| EP | 0658549 B1 | 5/2001 | |
| EP | 0971902 B1 | 12/2001 | |
| EP | 0324569 B1 | 10/2004 | |
| GB | 574995 | 1/1946 | |
| GB | 869169 | 5/1961 | |
| GB | 1040541 | 9/1966 | |
| JP | 60067463 | 4/1985 | |
| JP | 2002-522459 A | 7/2002 | |
| JP | 2009-505654 A | 2/2009 | |
| WO | 8300329 | 2/1983 | |
| WO | 8804297 | 6/1988 | |
| WO | 9105781 | 5/1991 | |
| WO | 9107089 | 5/1991 | |
| WO | 9113972 | 9/1991 | |
| WO | 9119806 | 12/1991 | |
| WO | 9211376 | 7/1992 | |
| WO | 9214827 | 9/1992 | |
| WO | 9215576 | 9/1992 | |
| WO | 9309099 | 5/1993 | |
| WO | 9510507 | 4/1995 | |
| WO | 9529899 | 11/1995 | |
| WO | 9641537 | 12/1996 | |
| WO | 9802526 | 1/1998 | |
| WO | 9802527 | 1/1998 | |
| WO | 00/08939 A1 | 2/2000 | |
| WO | 0230921 A1 | 4/2002 | |
| WO | 0236595 A2 | 5/2002 | |
| WO | 2005096818 A1 | 10/2005 | |
| WO | 2006008159 A1 | 1/2006 | |
| WO | 2007/005581 A2 | 1/2007 | |
| WO | 2007/024782 A2 | 3/2007 | |
| WO | WO 2007/149069 * | 12/2007 | A01H 5/00 |
| WO | WO 2007/149069 A2 * | 12/2007 | A01H 5/00 |
| WO | WO-2007149069 A2 * | 12/2007 | C12N 9/88 |
| WO | 2008124495 A2 | 10/2008 | |
| WO | 2009046334 A1 | 4/2009 | |
| WO | 2009046334 A4 | 4/2009 | |
| WO | 2009053058 A2 | 4/2009 | |
| WO | WO/2009/115237 * | 9/2009 | A01N 47/36 |
| WO | WO/2009/115237 A1 * | 9/2009 | A01N 47/36 |
| WO | WO2009115237 * | 9/2009 | A01N 47/36 |
| WO | WO-2009115237 A1 * | 9/2009 | A01N 47/36 |
| WO | 2012049266 A1 | 4/2012 | |
| WO | 2012049268 A1 | 4/2012 | |

OTHER PUBLICATIONS

Stougaard et al, Herbicide Resistant Mutants of Sugar Beet (*Beta vulgaris*), Abstract in Molecular Strategies for Crop Improvement, J. of Cell. Biochem. (1990) Supplement, Apr. 16-22, p. 310, Abstract No. R249; Listed in the IDS sumbitted on Oct. 30, 2013 as item XP-001028988.*

Stougaard et al, Herbicide Resistant Mutants of Sugarbeet (*Beta vulgaris*), Abstract in Molecular Strategies for Crop Improvement, J. of Cell. Biochem. (1990) Supplement, Apr. 16-22, p. 310, Abstract No. R249; Listed in the IDS submitted on Oct. 30, 2013 as item XP-001028988.*

Dexter, A. G., and Zollinger, R. K. 2001, "Weed control guide for sugarbeet." Sugarbeet Res. Ext. Rep 32: 3-34.*

Yu, Qin, and Stephen B. Powles. "Resistance to AHAS inhibitor herbicides: current understanding." Pest management science 70.9 (2014): 1340-1350.*

Sibony, Moshe, and Baruch Rubin. "Molecular basis for multiple resistance to acetolactate synthase-inhibiting herbicides and atrazine in *Amaranthus blitoides* (prostrate pigweed)." Planta 216.6 (2003): 1022-1027.*

Dexter, A., et al, 2001, Sugarbeet Res. Ext. Rep 32: 3-34.*

Alan G. Dexter, 2001, Sugarbeet Res. Ext. Rep 32: 3-34.*

Alan G. Dexter, 2001, Sugarbeet Res. Ext. Rep 32: 3-34 (Year: 2001).*

International Search Report for PCT/EP2011/067922 dated Dec. 27, 2011.

International Preliminary Report on Patentability for PCT/EP2011/067922 dated Apr. 25, 2013.

Elmo M. Beyer, Jr. et al., "Sulfonylureas in Herbicides: Chemistry, Degradation, and Mode of Action" 1988, 117-189.

David Chipman et al., "Biosynthesis of 2-aceto-2-hydroxy acids: acetolactate synthases and acetohydroxyacid synthases", Biochimica et Biophysica Acta 1385, 1998, 401-419.

Alan K. Chang et al., "Herbicide-resistant forms of *Arabidopsis thaliana* acetohydroxyacid synthase: characterization of the catalytic properties and sensitivity to inhibitors of four defined mutants", Biochem J. (1998) 333, 765-777.

(56) References Cited

OTHER PUBLICATIONS

Joseph W. Saunders et al., "Monogenic Dominant Sulfonylurea Resistance in Sugarbeet from Somatic Cell Selection", Crop Science 32:1357-1360 (1992).
R.G. Duggleby, "Structure and Properties of Acetohydroxyacid Synthase", Thiamine—Catalytic Mechanisms in Normal and Disease States, vol. 11, 251-274, (2004).
Entwicklungsstadien mono—und dikotyler Pflanzen, 2nd Edition, ed. Uwe Meier, 2001.
R.G. Duggleby et al., "Systematic characterization of mutations in yeast acetohydroxyacid synthase", Interpretation of herbicide-resistance data, European Journal of Biochemistry, 270, 2895-2904 (2003).
P. Langeluddeke et al., "Trials on the Influence of Air Humidity and Rainfall on the Efficacy of Glufosinate-Ammonium", Proc. EWRS Symp. Factors affecting herbicidal Activity and Selectivity, 227-232, 1988.
Ford Lloyd, "Genetics and Breeding of Sugar Beet", Sources of Genetic Variation, Genus Beta, Science Publishers, USA, pp. 25-33, 2005.
Growth stages of mono-and dicotyledonous plants, BBCH Monograph, Federal Biological Research Centre for Agriculture and Forestry, 2nd Edition, Edited by Uwe Meier, 2001.
Tsutomu Shimizu et al., "Acetolactate Synthase Inhibitors", Herbicide Classes in Development, 2002.
Georg Jander et al., "Ethylmethanesulfonate Saturation Mutagenesis in *Arabidopsis* to Determine Frequency of Herbicide Resistance", Plant Physiology, vol. 131, pp. 139-146, Jan. 2003.
R.G. Duggleby et al., "Acetohydroxyacid Synthase", Journal of Biochemistry and Molecular Biology, vol. 33, No. 1, pp. 1-36, Jan. 2000.
Siew Siew Pang et al., "Molecular Basis of Sulfonylurera Herbicide Inhibition of Acetohydroxyacid Synthase", The Journal of Biological Chemistry, vol. 278, No. 9, Issue of Feb. 28, pp. 7639-7644, 2003.
Sun-Mi Jung et al., "Amino acid residues conferring herbicide resistance in tobacco acetohydroxy acid synthase", Biochem. J. (2004) 383, 53-61.
William A. Kleschick et al., "DE-498, a New Acetolactate Synthase Inhibiting Herbicide with Multicrop Selectivity", J. Agric. Food Chem., vol. 40, pp. 1083-1085, 1992.
Jiro Hattori et al., "An Acetohydroxy acid synthase mutant reveals a single site involved in multiple herbicide resistance", Molecular and General Genetics, 246, pp. 419-425, 1995.
Siyuan Tan et al., "Imidazolinone-tolerant crops: history, current status and future", Pest Management Science, 61, pp. 246-257, 2005.
Uwe Sonnewald et al., "Transgenic tobacco plants expressing yeast-derived invertase in either the cytosol, vacuole or apoplast: a powerful tool for studying sucrose metabolism and sink/source interactions", The Plant Journal 1(1), pp. 95-106, (1991).
R.G. Duggleby et al., "Structure and mechanism of inhibition of plant acetohydroxyacid synthase", Plant Physiology and Biochemistry 46, pp. 309-324, (2008).
R. Pontzen, "Propoxycarbazone-sodium (BAY MKH 6561): systemic properties and basis of selectivity in wheat", Pflanzenschutz-Nachrichten Bayer, vol. 55, pp. 37-52, (2002).
Frank P. Wolter et al., "rbcS genes in Solanum tuberosum: Conservation of transit peptide and exon shuffling during evolution", Proc. Natl. Acad. Sci. USA, vol. 85, pp. 846-850, Feb. 1988.
Proceedings, South. Weed Sci. Soc. 45, 341 (1992).
Juergen Falbe et al., "Roempp-Chemie-Lexikon", 9th Edition, vol. 2, 1343, (1995).

Dale L. Shaner et al., "Short Communication, Imidazolinones, Potent Inhibitors of Acetohydroxyacid Synthase", Plant Physiol., 76, pp. 545-546, (1984).
Dale L. Shaner et al., "The Imidazolinone Herbicides", CRC Press, Table of Contents, (1991).
Tsutomu Shimizu, "Action Mechanism of Pyrimidinyl Carboxy Herbicides", Pesticide Science, Life Science Research Institute, Kumiai Chemical Industry Co., Ltd., 22, pp. 245-246, (1997).
Hans-Peter Braun et al., "The general mitochondrial processing peptidase from potato is an integral part of cytochrome c reductase of the respiratory chain", The EMBO Journal, vol. 11, No. 9, pp. 3219-3227, (1992).
Judith M. Kolkman et al., "Acetohydroxyacid synthase mutations conferring resistance to imidazolinone or sulfonylurea herbicides in sunflower", Theoretical and Applied Genetics, 109: pp. 1147-1159, (2004).
Paul Christou, "Transformation technology", Trends in Plant Science, vol. 1, No. 12, pp. 423-431, (1996).
H.E. Umbarger, "Amino Acid Biosynthesis and its Regulation", Annu. Rev. Biochem. 47, pp. 533-606, (1978).
Weed Research, vol. 26, pp. 441-445, (1986).
P.L. Orwick et al., "A New Broad Spectrum Herbicide for Soybeans: Greenhouse Studies", Weed Science Society, 36th Annual Meeting, pp. 90-91, (1983).
Weed Science Society Meeting (1984), 18 (Modern Agrochemicals, 2004), pp. 14-15.
Patrick J. Tranel et al., "Resistance of weeds to ALS-inhibiting herbicides: what have we learned?", Weed Science 50 (2002), pp. 700-712.
Peter Stougaard et al., "Herbicide Resistant Mutants of Sugar Beet (*Beta vulgaris*)", DANISCO A/S, Biotechnology Research Division, J. Cell Biochem., Suppl. 14E, 1990, XP-001028988.
Terry R. Wright et al., "In vitro and whole-plant magnitude and cross-resistance characterization of two imidazolinone-resistant sugarbeet (*Beta vulgaris*) somatic cell selections", Weed Science, 46:24-29. 1998, XP-001029322.
Moshe Sibony et al., "Molecular basis for multiple resistance to acetolactate synthase-inhibiting herbicides and atrazine in *Amaranthus blitoides* (prostrate pigweed)", Planta (2003) 216: 1022-1027, XP-002631640.
Narendra Yadav et al., "Single amino acid substitutions in the enzyme acetolactate synthase confer resistance to the herbicide sulfometuron methyl", Proc. Natl. Acad. Sci. USA, vol. 83, pp. 4418-4422, Jun. 1986, Genetics.
International Search Report Based on Application No. PCT/EP2011/067922 dated Dec. 27, 2011.
Chaleff et al., "Direct selection in vitro for herbicide-resistant mutants of Nicotiana tabacum." Proc. Natl. Acad. Sci., vol. 75, No. 10, pp. 5104-5107, Oct. 1978, Genetics.
Mezei et al., "Sugar Beet Micropropagation." Biotechnol. & Biotechnol. Eq. vol. 20, No. 1, pp. 9-14, 2006.
Tardif et al., "A mutation in the herbicide target site acetohydroxyacid synthase produces morphological and structural alterations and reduces fitness in Amaranthus powellii." New Phytologist, vol. 169, pp. 251-264, 2006.
"Notice of opposition to a European patent," for EP2627183, dated Jun. 29, 2018.
Bernasconi, et al., "A Naturally Occurring Point Mutation Confers Broad Range Tolerance to Herbicides That Target Acetolactate Synthase," J. Biol. Chem., (1995), vol. 270, No. 29: 17381-17385.
Anderson, et al., "Herbicide-tolerant mutants of corn," Genome, (1989), vol. 31: 994-999.
Swanson, et al., "Microspore mutagenesis and selection: Canola plants with field tolerance to the imidazollinones," Theor Appl Genet, (1989), vol. 78: 525-530.

* cited by examiner

METHODS OF USING ALS INHIBITOR HERBICIDES FOR CONTROL OF UNWANTED VEGETATION IN ALS INHIBITOR HERBICIDE TOLERANT BETA VULGARIS PLANTS

CROSS REFERENCE TO RELATED APPLICATIONS

This application is a § 371 National Stage Application of PCT/EP2011/067922 filed Oct. 13, 2011, which claims priority to European Application No. 10187759.5 filed Oct. 15, 2010 and U.S. Provisional Application No. 61/394,469, filed Oct. 19, 2010.

BACKGROUND OF THE INVENTION

Field of the Invention

Description of Related Art

The present invention relates to the technical field of crop protection by using ALS (acetolactate synthase; also known as AHAS (acetohydroxyacid synthase; EC 2.2.1.6; formerly EC 4.1.3.18)) inhibitor herbicides against unwanted vegetation in areas of growing *Beta vulgaris* plants, preferably sugar beet, that are tolerant against ALS inhibitor herbicides by comprising a mutation in the codon 1705-1707 of an endogenous ALS gene thereby encoding an ALS polypeptide having an amino acid that is different from the naturally occurring tryptophan at position 569.

Cultivated forms of *Beta vulgaris* (as defined in Ford-Lloyd (2005) Sources of genetic variation, Genus *Beta*. In: Biancardi E, Campbell L G, Skaracis G N, De Biaggi M (eds) Genetics and Breeding of Sugar Beet. Science Publishers, Enfield (NH), USA, pp 25-33) are important agricultural crops in temperate and subtropical regions. For example, about 20% of the world sugar production is based on sugar beet. Because beet seedlings and juvenile plants during their first 6-8 weeks of their life are susceptible for strong competition caused by fast growing weeds, which outcompete the young crop plants, reliable weed control measures are imperative in these crop areas.

Since more than 40 years, herbicides are the preferred tools to control weeds in sugar beet (*Beta vulgaris* subsp. *vulgaris* var *altissima*). The products used for this purpose, namely phenmedipham, desmediphan, ethofumesate, and metamitron allow to suppress weeds in sugar beet fields without damaging the crop. Nevertheless, under adverse environmental conditions the efficacy of these products leaves room for improvements, especially if noxious weeds like *Chenopodium album, Amaranthus retroflexus* and/or *Fallopia convolvulus* germinate over an extended period of time.

The ALS/AHAS enzyme is present in bacteria, fungi, and plants and from various organisms protein isolates have been obtained and their corresponding amino acid/nucleic acid sequences as well as their biochemical characteristics have been determined/characterized (for review, see at Umbarger, H. E., Annu. Rev. Biochem. (1978), 47, 533-606; Chiman, D. M. et al., Biochim. Biophys. Acta (1998), 1385, 401-419; Duggleby, R. G., and Pang, S. S., J. Biochem. Mol. Biol. (2000), 33, 1-36; Duggleby, R. G. (Structure and Properties of Acetohydroxyacid Synthase in Thiamine: Catalytic Mechanisms in Normal and Disease States, Vol 11, Marcel Dekker, New York, 2004, 251-274,)

The use of herbicidal compounds belonging to the class of ALS inhibitors, like (a) sulfonylurea herbicides (Beyer E. M et al. (1988), Sulfonylureas in Herbicides: Chemistry, Degradation, and Mode of Action; Marcel Dekker, New York, 1988, 117-189), (b) sulfonylaminocarbonyltriazolinone herbicides (Pontzen, R., Pflanz.-Nachrichten Bayer, 2002, 55, 37-52), (c) imidazolinone herbicides (Shaner, D. L., et al., Plant Physiol., 1984, 76, 545-546; Shaner, D. L., and O'Connor, S. L. (Eds.) The Imidazolinone Herbicides, CRC Press, Boca Rato, Fla., 1991), (d) triazolopyrimidine herbicides (Kleschick, W. A. et al., Agric. Food Chem., 1992, 40, 1083-1085), and (e) pyrimidinyl(thio)benzoate herbicides (Shimizu, T. J., Pestic. Sci., 1997, 22, 245-256; Shimizu, T. et al., Acetolactate Syntehase Inhibitors in Herbicide Classes in Development, Boger, P., Wakabayashi. K., Hirai, K., (Eds.), Springer Verlag, Berlin, 2002, 1-41) for the control of unwanted vegetation in various crop cultures is well known in agriculture.

A broad variety of ALS/AHAS inhibitor herbicides enable a farmer to control a wide range of weed species independently of their growth stages, but these highly efficient herbicides cannot be used in *Beta vulgaris*, preferably sugar beet, because *Beta vulgaris*, especially conventional sugar beet plants/commercial sugar beet varieties are highly susceptible against/affected by these ALS inhibitor herbicides.

Nevertheless, these ALS inhibitor herbicides show an excellent herbicidal activity against broadleaf and grass weed species. The first herbicides based on ALS inhibitors were developed for their use in agriculture already 30 years ago. Nowadays, active ingredients of this class exhibit a strong weed control and are widely used in maize and cereals as well as in dicot crops, except *Beta vulgaris*, preferably sugar beet.

By now, there is only one commercially available product based on a sulfonylurea herbicide, i.e. Debut® (component (A) 50% triflusulfuron-methyl+component (B) a specific formulation compound, i.e. a specific adjuvant) which can be used in sugar beet in post emergent application, but it requires the application at a very early leaf stage of the weeds to be treated and also show severe gaps in the treatment of serious weeds growing in sugar beet plantings. This sulfonylurea is not tolerated by but degraded in the sugar beet plants.

Another, more reliable and more flexible way to obtain *Beta vulgaris*, preferably sugar beet plants that stand an ALS inhibitor herbicide treatment is to generate mutants that are sufficiently tolerant to agronomically useful/necessary quantities of ALS inhibitor herbicides in order to control serious unwanted vegetation in *Beta vulgaris*, preferably sugar beet plantings.

Since ALS inhibitor herbicides were introduced into agriculture it was observed that susceptible plant species, including naturally occurring weeds, occasionally develop spontaneous tolerance to this class of herbicides. Single base pair substitutions at specific sites of the ALS gene usually lead to more or less resistant ALS enzyme variants which show different levels of inhibition by the ALS inhibitor herbicides. Plants conferring mutant ALS alleles therefore show different levels of tolerance to ALS inhibitor herbicides, depending on the chemical structure of the ALS inhibitor herbicide and the site of the point mutation(s) in the ALS gene and the hereby encoded ALS protein.

Several mutants (naturally occurring in weeds but also artificially induced in crops by either mutation or transgenic approaches) of the ALS conferring tolerance to one or more chemicals defined under the above given ALS inhibitor herbicide classes/groups are known at various parts of the enzyme (i.e. in the α-, β-, and γ-domain of the ALS h are known and have been identified in various organisms, including plants (U.S. Pat. No. 537,882; Duggleby, R. G. et al., (2008), Plant Physiol. and Biochem., pp 309-324; Siyuan, T. et al. (2005), Pest Management Sci., 61, pp 246-257; Jung, S. (2004) Biochem J., pp 53-61; Kolkman, J. M. (2004), Theor. Appl. Genet., 109, pp 1147-1159; Duggleby, R. G. et al (2003), Eur. J. Biochem., 270, pp 1295-2904; Pang, S. S., et al. (2003), J. Biol. Chem., pp 7639-7644); Yadav, N. et al., (1986), Proc. Natl. Acad. Sci., 83, pp 4418-4422), Jander G. et al. (2003), Plant Physiol., 131, pp. 139-146); Tranel, P. J., and Wright, T. R. (2002), Weed Science, 50, pp 700-712); Chang, A. K., and Duggleby, R. G. (1998), Biochem J., 333, pp. 765-777).

Crop plants conferring mutant ALS alleles do show different levels of tolerance to ALS inhibitor herbicides, depending on the chemical structure of the ALS inhibitor herbicide and the site of the point mutation in the ALS gene.

For example, Hattori et al. (1995), Mol. Gen. Genet. 246: 419-425, describes a single mutation in the Trp 557 codon in a *Brassica napus* cell line (according to the numbering of the *Arabidopsis thaliana* sequence that is used in the literature in order to compare all ALS/AHAS mutants this refers to position "574")—which equals position 569 of the beet ALS polypeptide sequence. These authors observed resistance to several members of sub-classes of ALS inhibitor herbicides, like sulfonylureas, imidazolinones and triazolopyrimidines.

EP-A-0360750 describes the production of ALS inhibitor herbicide tolerant plants by producing an increased amount of the attacked ALS inside the plant. Such plants show an increased tolerance against certain sulfonyureas, like chlorsulfuron, sulfometuron-methyl, and triasulfuron.

U.S. Pat. No. 5,198,599 describes sulfonylurea and imidazolinone tolerant plants that have been obtained via a selection process and which show a tolerance against chlorsulfuron, bensulfuron, chlorimuron, thifensulfuron and sulfometuron.

Furthermore, U.S. Pat. Nos. 5,013,659, 5,141,870, and 5,378,824 describe the production of transgenic sugarbeet plants by introducing a modified yeast ALS gene into such sugarbeet plants.

In addition, Saunders et al. (Crop Science, 1992, 32, 1317-1320) disclose sulfonylurea tolerant sugar beet plants that were obtained via somaclonal cell selection but these authors neither showed up any biological data concerning the level of tolerance of such plants against ALS inhibitor herbicide treatment nor did they demonstrate genetically stable mutants obtained from cultures in which these mutations have been generated.

Stougaard et al. (1990), J. Cell Biochem., Suppl. 14E, 310 describe the isolation of ALS mutants in a tetraploid sugar beet cell culture. Two different ALS genes (ALS I and ALS II) were isolated which differed at amino acid position 37 only. Mutant 1 contained in its ALS I gene 2 mutations, while mutant 2 contained 3 mutations in its ALS II gene. After the mutations were separated to resolve which mutation would confer resistance against an ALS inhibitor, it was revealed that ALS synthesized from a recombinant *E. coli* was herbicide resistant if it contained a point mutation in the Trp 574 codon (according to the numbering of the *Arabidopsis thaliana* sequence that is used in the literature in order to compare all ALS mutants)—which equals position 569 of the beet ALS amino acid sequence, leading to a replacement of the amino acid "Trp" by the amino acid "Leu". Stougaard et al did not show in sugar beet that the mutation at position 569 of any of the sugar beet ALS genes is sufficient in order to obtain an agronomically acceptable level of tolerance to ALS inhibitor herbicides. Moreover, Stougaard et al did not regenerate or handle sugar beet plants comprising a mutation, including Trp→Leu mutation at position 569 of sugar beet ALS.

Knowing this, Stougaard et al. constructed plant transformation vectors containing different ALS genes for use in plant transformation. However, up to now, no further data—especially not concerning the effects of the application of ALS inhibitor herbicides to plants and/or agricultural areas comprising this mutation in *Beta vulgaris* plants have been disclosed by these or other authors either in genetically engineered or mutant plants over more than 20 years, thereafter.

Additionally, beet mutants were described conferring a point mutation in the Ala 122 codon which led to a certain tolerance to the ALS inhibitor herbicide subclass of imidazolinones (WO 98/02526) but which is not sufficient for weed control in agricultural application schemes. No crosstolerance to other ALS inhibitor herbicide classes were described by employing this mutant. Furthermore, beet plants conferring a second point mutation in the Pro 197 codon showed a moderate tolerance to ALS inhibitor herbicides belonging to members of the subclass of sulfonylurea herbicides. Also double mutants of these two were described (WO 98/02527). However, none of these mutants were used for the market introduction of beet varieties because the level of herbicide tolerance to ALS inhibitor herbicides was not sufficiently high in these mutants to be exploited agronomically.

WO 2008/124495 discloses ALS double and triple mutants. According to WO 2009/046334, specific mutations in the ALS gene were provided. However, agronomically exploitable *Beta vulgaris* mutants containing such mutations according to WO 2009/046334 and also showing a sufficient tolerance to any kind of ALS inhibitor herbicides of various ALS inhibitor herbicide classes have not been obtained/described by now.

All these sugar beet mutants do not show a reliable tolerance against various classes of the ALS inhibitor herbicides, and—even worse—they do not show a tolerance level that is useful at agronomic application rates against any kind of ALS inhibitor herbicides.

As it relates to the compounds known acting as ALS inhibitor herbicides, these can be grouped in several classes.

Compounds from the group of the (sulfon)amides are already known as herbicidally active compounds for controlling unwanted vegetation; see, for example, EP 239414, U.S. Pat. No. 4,288,244, DE 3303388, U.S. Pat. Nos. 5,457,085, 3,120,434, 3,480,671, EP 206251, EP 205271, U.S. Pat. Nos. 2,556,664, 3,534,098, EP 53011, U.S. Pat. No. 4,385,927, EP 348737, DE 2822155, U.S. Pat. No. 3,894,078, GB 869169, EP 447004, DE 1039779, HU 176582, U.S. Pat. No. 3,442,945, DE 2305495, DE 2648008, DE 2328340, DE 1014380, HU 53483, U.S. Pat. No. 4,802,907, GB 1040541, U.S. Pat. Nos. 2,903,478, 3,177,061, 2,695,225, DE 1567151, GB 574995, DE 1031571, U.S. Pat. No. 3,175,897, JP 1098331, U.S. Pat. No. 2,913,327, WO 8300329, JP 80127302, DE 1300947, DE 2135768, U.S. Pat. Nos. 3,175,887, 3,836,524, JP 85067463, U.S. Pat. No. 3,582,314, US 53330821, EP 131258, U.S. Pat. Nos. 4,746,353, 4,420,325, 4,394,506, 4,127,405, 4,479,821, 5,009,699, EP 136061, EP 324569, EP 184385, WO 2002030921, WO 09215576, WO 09529899, U.S. Pat. No. 4,668,277, EP 305939, WO 09641537, WO 09510507, EP 7677, CN 01080116, U.S. Pat. No. 4,789,393, EP 971902, U.S. Pat. No. 5,209,771, EP 84020, EP 120814, EP 87780, WO 08804297, EP 5828924, WO 2002036595, U.S. Pat. No. 5,476,936, WO 2009/053058 and the literature cited in the publications mentioned above.

Compounds from the group of the imidazolinones are already known as herbicidally active compounds for controlling unwanted vegetation; see, for example Proc. South. Weed Sci. Soc. 1992. 45, 341, Proc. South. Weed Sci. Soc. Annu. Mtg. 36th, 1983, 29, Weed Sci. Soc. Annu. Mtg. 36th, 1983, 90-91, Weed Sci. Soc. Mtg., 1984, 18, Modern Agrochemicals, 2004, 14-15.

Compounds from the group of the pyrimidinyl(thio)benzoates are already known as herbicidally active compounds for controlling unwanted vegetation; see, for example U.S. Pat. No. 4,906,285, EP 658549, U.S. Pat. No. 5,118,339, WO 91/05781, U.S. Pat. No. 4,932,999, and EP 315889.

Compounds from the group of the sulfonanilides are already known as herbicidally active compounds for controlling unwanted vegetation; see, for example WO 93/09099, WO 2006/008159, and WO 2005/096818.

All publications and patents cited in this disclosure are incorporated by reference in their entirety. To the extent the material incorporated by reference contradicts or is inconsistend with this specification, the specification will supersede any such material.

In view of the fact that, for example, sugar beet accounts for about 20% of the world sugar beet production, it would be highly desirable to have available a weed control system that enables the efficient control of highly potent and serious weeds. It would thus be highly desirable to use one or more ALS inhibitor herbicides for control of unwanted vegetation in *Beta vulgaris* plants, preferably sugar beet plants which are tolerant to such ALS inhibitor herbicides.

This problem was solved according to present invention.

SUMMARY

The present invention relates to the use of one or more ALS inhibitor herbicide(s) belonging to one or various ALS inhibitor herbicide class(es) for controlling unwanted vegetation in *Beta vulgaris*, preferably in sugar beet growing areas in which the *Beta vulgaris* plants, preferably sugar beet plants comprise a mutation in codon 1705-1707 of an endogenous acetolactate synthase (ALS) gene encoding an ALS protein containing an amino acid that is different from tryptophan at position 569, preferably the tryptophan of the wild-type ALS protein is substituted by a leucine at position 569.

DETAILED DESCRIPTION OF A PREFERRED EMBODIMENT

Seeds of sugar beet plants comprising such mutation and which can be employed according to present invention have been deposited with the NCIMB, Aberdeen, UK, under Number NCIMB 41705 on Mar. 12, 2010.

More preferably, the present invention relates to the use of one or more ALS inhibitor herbicide(s) in *Beta vulgaris* mutants, preferably sugar beet mutants, comprising a mutation in codon 1705-1707 of an endogenous acetolactate synthase (ALS) gene encoding an ALS protein containing an amino acid that is different from tryptophan at position 569, preferably the tryptophan of the wild-type ALS protein is substituted by a leucine at position 569 and wherein the ALS inhibitor herbicide(s) belong to:
the group of the (sulfon)amides (group (A)) consisting of:
the subgroup (A1) of the sulfonylureas, consisting of:

amidosulfuron [CAS RN 120923-37-7] (=A1-1);
azimsulfuron [CAS RN 120162-55-2] (=A1-2);
bensulfuron-methyl [CAS RN 83055-99-6] (=A1-3);
chlorimuron-ethyl [CAS RN 90982-32-4] (=A1-4);
chlorsulfuron [CAS RN 64902-72-3] (=A1-5);
cinosulfuron [CAS RN 94593-91-6] (=A1-6);
cyclosulfamuron [CAS RN 136849-15-5] (=A1-7);
ethametsulfuron-methyl [CAS RN 97780-06-8] (=A1-8);
ethoxysulfuron [CAS RN 126801-58-9] (=A1-9);
flazasulfuron [CAS RN 104040-78-0] (=A1-10);
flucetosulfuron [CAS RN 412928-75-7] (=A1-11);
flupyrsulfuron-methyl-sodium [CAS RN 144740-54-5] (=A1-12);
foramsulfuron [CAS RN 173159-57-4] (=A1-13);
halosulfuron-methyl [CAS RN 100784-20-1] (=A1-14);
imazosulfuron [CAS RN 122548-33-8] (=A1-15);
iodosulfuron-methyl-sodium [CAS RN 144550-36-7] (=A1-16);
mesosulfuron-methyl [CAS RN 208465-21-8] (=A1-17);
metsulfuron-methyl [CAS RN 74223-64-6] (=A1-18);
monosulfuron [CAS RN 155860-63-2] (=A1-19);
nicosulfuron [CAS RN 111991-09-4] (=A1-20);
orthosulfamuron [CAS RN 213464-77-8] (=A1-21);
oxasulfuron [CAS RN 144651-06-9] (=A1-22);
primisulfuron-methyl [CAS RN 86209-51-0] (=A1-23);
prosulfuron [CAS RN 94125-34-5] (=A1-24);
pyrazosulfuron-ethyl [CAS RN 93697-74-6] (=A1-25);
rimsulfuron [CAS RN 122931-48-0] (=A1-26);
sulfometuron-methyl [CAS RN 74222-97-2] (=A1-27);
sulfosulfuron [CAS RN 141776-32-1] (=A1-28);
thifensulfuron-methyl [CAS RN 79277-27-3] (=A1-29);
triasulfuron [CAS RN 82097-50-5] (=A1-30);
tribenuron-methyl [CAS RN 101200-48-0] (=A1-31);
trifloxysulfuron [CAS RN 145099-21-4] (sodium) (=A1-32);
triflusulfuron-methyl [CAS RN 126535-15-7] (=A1-33);
tritosulfuron [CAS RN 142469-14-5] (=A1-34);
NC-330 [CAS RN 104770-29-8] (=A1-35);
NC-620 [CAS RN 868680-84-6] (=A1-36);
TH-547 [CAS RN 570415-88-2] (=A1-37);
monosulfuron-methyl [CAS RN 175076-90-1] (=A1-38);
2-iodo-N-[(4-methoxy-6-methyl-1,3,5-triazinyl)carbamoyl]benzene-sulfonamide (=A1-39);
a compound of the general formula (I)

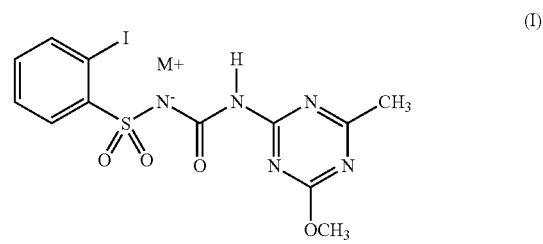

where M+ denotes the respective salt of the compound (I), i.e. its lithium salt (=A1-40); its sodium salt (=A1-41); its potassium salt (=A1-42); its magnesium salt (=A1-43); its calcium (=A1-44); its ammonium salt (=A1-45); its methylammonium salt (=A1-46); its dimethylammonium salt (=A1-47); its tetramethylammonium salt (=A1-48); its ethylammonium salt (=A1-49); its diethylammonium salt (=A1-50); its tetraethylammonium salt (=A1-51); its propylammonium salt (=A1-52); its tetrapropylammonium salt (=A1-53); its isopropylammonium salt (=A1-54); its diisopropylammonium salt (=A1-55); its butylammonium salt (=A1-56); its tetrabutylammonium salt (=A1-57); its (2-hydroxyeth-1-yl)ammonium salt (=A1-58); its bis-N,N-(2-hydroxyeth-1-yl)ammonium salt (=A1-59); its tris-N,N,N-(2-hydroxyeth-1-yl)ammonium salt (=A1-60); its 1-phenylethylammonium salt (=A1-61); its 2-phenylethylammonium salt (=A1-62); its trimethylsulfonium salt (=A1-63); its trimethyloxonium salt (=A1-64); its pyridinium salt (=A1-65); its 2-methylpyridinium salt (=A1-66); its 4-methylpyridinium salt (=A1-67); its 2,4-dimethylpyridinium salt (=A1-68); its 2,6-dimethylpyridinium salt (=A1-69); its piperidinium salt (=A1-70); its imidazolium salt (=A1-71); its morpholinium salt (=A1-72); its 1,5-diazabicyclo[4.3.0]non-7-enium salt (=A1-73); its 1,8-diazabicyclo[5.4.0]undec-7-enium salt (=A1-74);

or a compound of the formula (II) or salts thereof

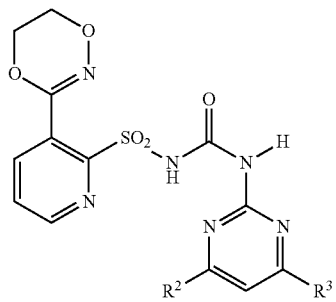
(II)

with $R^2$, and $R^3$ having the meaning as defined in the below table

| Compound | $R^2$ | $R^3$ |
|---|---|---|
| A1-75 | OCH$_3$ | OC$_2$H$_5$ |
| A1-76 | OCH$_3$ | CH$_3$ |
| A1-77 | OCH$_3$ | C$_2$H$_5$ |
| A1-78 | OCH$_3$ | CF$_3$ |
| A1-79 | OCH$_3$ | OCF$_2$H |
| A1-80 | OCH$_3$ | NHCH$_3$ |
| A1-81 | OCH$_3$ | N(CH$_3$)$_2$ |
| A1-82 | OCH$_3$ | Cl |
| A1-83 | OCH$_3$ | OCH$_3$ |
| A1-84 | OC$_2$H$_5$ | OC$_2$H$_5$ |
| A1-85 | OC$_2$H$_5$ | CH$_3$ |
| A1-86 | OC$_2$H$_5$ | C$_2$H$_5$ | or the compound of formula (III) (=A1-87), i.e. the sodium salt of compound (A1-83)

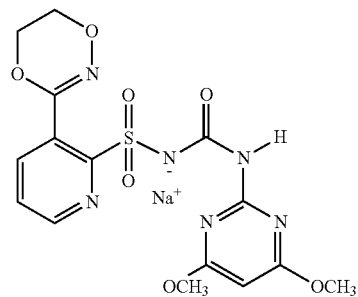
(III)

or the compound of formula (IV) (=A1-88), i.e. the sodium salt of compound (A1-82)

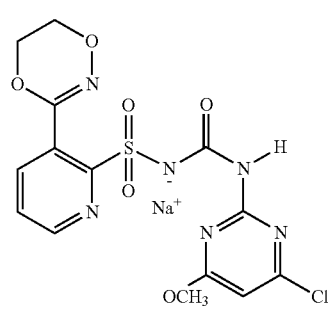
(IV)

the subgroup of the sulfonylaminocarbonyltriazolinones (subgroup ((A2)), consisting of:
flucarbazone-sodium [CAS RN 181274-17-9] (=A2-1);
propoxycarbazone-sodium [CAS RN 181274-15-7] (=A2-2);
thiencarbazone-methyl [CAS RN 317815-83-1] (=A2-3);
the subgroup of the triazolopyrimidines (subgroup (A3)), consisting of:
cloransulam-methyl [147150-35-4] (=A3-1);
diclosulam [CAS RN 145701-21-9] (=A3-2);
florasulam [CAS RN 145701-23-1] (=A3-3);
flumetsulam [CAS RN 98967-40-9] (=A3-4);
metosulam [CAS RN 139528-85-1] (=A3-5);
penoxsulam [CAS RN 219714-96-2] (=A3-6);
pyroxsulam [CAS RN 422556-08-9] (=A3-7);
the subgroup of the sulfonanilides (subgroup (A4)), consisting of:
compounds or salts thereof from the group described by the general formula (I):

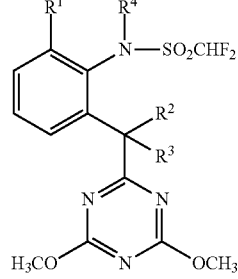
(V)

in which
$R^1$ is halogen, preferably fluorine or chlorine,
$R^2$ is hydrogen and $R^3$ is hydroxyl or
$R^2$ and $R^3$ together with the carbon atom to which they are attached are a carbonyl group C=O and
$R^4$ is hydrogen or methyl;

and more especially compounds of the below given chemical structure (A4-1) to (A4-8)

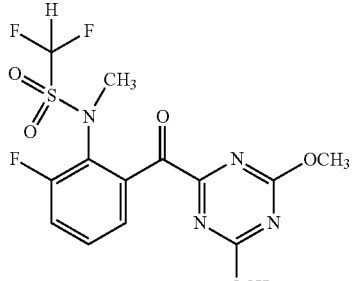
(A4-1)

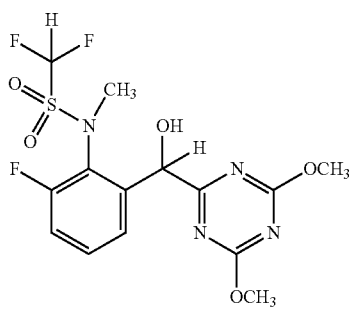
(A4-2)

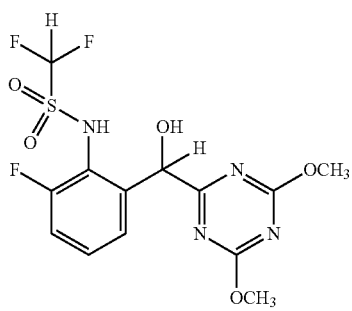
(A4-3)

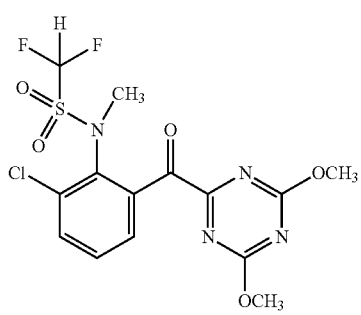
(A4-4)

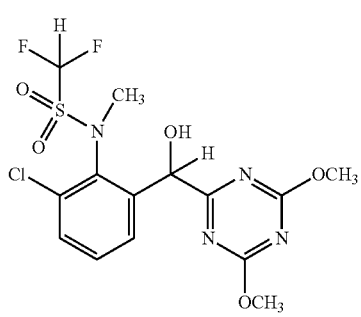
(A4-5)

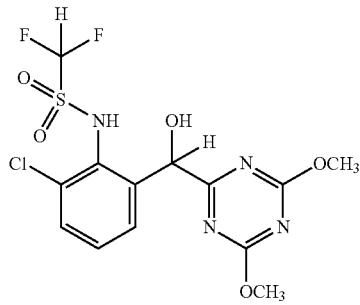
(A4-6)

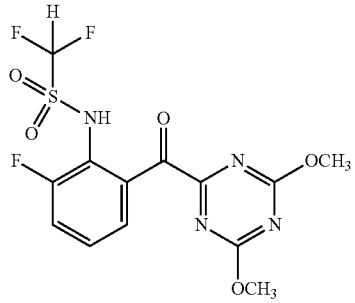
(A4-7)

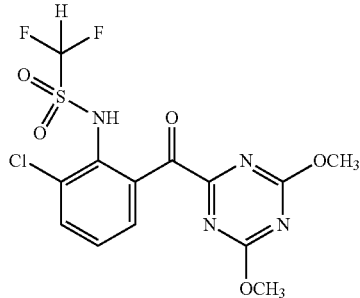
(A4-8)

the group of the imidazolinones (group (B1)), consisting of:
  imazamethabenzmethyl [CAS RN 81405-85-8] (=B1-1);
  imazamox [CAS RN 114311-32-9] (=B1-2);
  imazapic [CAS RN 104098-48-8] (=B1-3);
  imazapyr [CAS RN 81334-34-1] (=B1-4);
  imazaquin [CAS RN 81335-37-7] (=B1-5);
  imazethapyr [CAS RN 81335-77-5] (=B1-6);
  SYP-298 [CAS RN 557064-77-4] (=B1-7);
  SYP-300 [CAS RN 374718-10-2] (=B1-8).
the group of the pyrimidinyl(thio)benzoates (group (C)), consisting of:
  the subgroup of the pyrimidinyloxybenzoeacids (subgroup (C1)) consisting of:
    bispyribac-sodium [CAS RN 125401-92-5] (=C1-1);
    pyribenzoxim [CAS RN 168088-61-7] (=C1-2);
    pyriminobac-methyl [CAS RN 136191-64-5] (=C1-3);
    pyribambenz-isopropyl [CAS RN 420138-41-6] (=C1-4);
    pyribambenz-propyl [CAS RN 420138-40-5] (=C1-5);
  the subgroup of the pyrimidinylthiobenzoeacids (subgroup (C2)), consisting of:
    pyriftalid [CAS RN 135186-78-6] (=C2-1);
    pyrithiobac-sodium [CAS RN 123343-16-8] (=C2-2).
In this context, "tolerance" or "tolerant" means that the application of one or more ALS inhibitor herbicide(s) belonging to any of the above defined groups (A), (B), (C) does not show any apparent effect(s) concerning the physiological functions/phytotoxicity when applied to the respective Beta vulgaris plant, especially sugar beet containing an ALS polypeptide comprising a mutation at position 569 and whereas the application of the same amount of the respective ALS inhibitor herbicide(s) on non-tolerant Beta vulgaris plants leads to significant negative effects concerning plant growth, its physiological functions or shows phytotoxic symptoms. Qualtity and quantity of the observed effects may depend on the chemical composition of the respective ALS inhibitor heribicide(s) applied, dose rate and timing of the application as well growth conditions/stage of the treated plants.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. The word "comprise" and its variations on the one side and the word "contain" and its analogous variations on the other side can be used interchangeably throughout this specification and the corresponding claims without a preference given to any of them.

When used herein, the term "transgenic" or "genetically modified" means that a gene—which can be of the same or a different species—has been introduced via an appropriate biological carrier, like *Agrobacterium tumefaciens* or by any other physical means, like protoplast transformation or particle bombardment, into a plant and which gene is able to be expressed in the new host environment, namely the genetically modified organism (GMO).

In accordance to the before definition, the term "non-transgenic" or "non-genetically modified" means exactly the contrary, i.e. that no introduction of the respective gene has occurred via an appropriate biological carrier or by any other physical means. However, a mutated gene can be transferred through pollination, either naturally or via a breeding process to produce another non-transgenic plant concerning this specific gene.

An "endogenous" gene means a gene of a plant which has not been introduced into the plant by genetic engineering techniques.

An "amino acid different from tryptophan" (indicated by "Trp" in the three letter code or "W" in the equivalently used one letter code) includes any naturally-occurring amino acid different from tryptophan. These naturally-occurring amino acids include alanine (A), arginine (R), asparagine (N), aspartate (D), cysteine (C), glutamine (Q), glutamate (E), glycine (G), histidine (H), isoleucine (I), leucine (L), lysine (K), methionine (M), phenylalanine (F), proline (P), serine (S), threonine (T), tyrosine (Y) or valine (V).

However, preferably, the amino acid different from tryptophan (belonging to the group of neutral-polar amino acids) at position 569 of the ALS protein is an amino acid with physico-chemical properties different from tryptophan, i.e. belonging to any of the amino acids showing neutral-nonpolar, acidic, or basic properties. More preferably, the amino acid different from tryptophan is selected from the group consisting of alanine, glycine, isoleucine, leucine, methionine, phenylalanine, proline, valine, and arginine.

Even more preferably, said amino acid is a neutral-nonpolar amino acid such as alanine, glycine, isoleucine, leucine, methionine, phenylalanine, proline or valine. Particularly preferred said amino acid is alanine, glycine, isoleucine, leucine, valine. Even more preferred is glycine and leucine.

Most preferably, it is leucine.

The "CAS RN" stated in square brackets behind the names (common names) mentioned under groups A to C corresponds to the "chemical abstract service registry number", a customary reference number which allows the substances named to be classified unambiguously, since the "CAS RN" distinguishes, inter alia, between isomers including stereoisomers.

ALS inhibitor herbicides which are preferably used for control of unwanted vegetation in *Beta vulgaris*, preferably sugar beet growing areas in which *Beta vulgaris*, preferably sugar beet plants contain an ALS protein encoded by an endogenous ALS gene comprising an amino acid different from tryptophan at position 569 and thereby providing tolerance against the ALS inhibitor herbicide(s) according to this invention belonging to group (A) are:
  amidosulfuron [CAS RN 120923-37-7] (=A1-1);
  chlorimuron-ethyl [CAS RN 90982-32-4] (=A1-4);
  ethametsulfuron-methyl [CAS RN 97780-06-8] (=A1-8);
  ethoxysulfuron [CAS RN 126801-58-9] (=A1-9);
  flupyrsulfuron-methyl-sodium [CAS RN 144740-54-5] (=A1-12);
  foramsulfuron [CAS RN 173159-57-4] (=A1-13);
  iodosulfuron-methyl-sodium [CAS RN 144550-36-7] (=A1-16);
  mesosulfuron-methyl [CAS RN 208465-21-8] (=A1-17);
  metsulfuron-methyl [CAS RN 74223-64-6] (=A1-18);
  monosulfuron [CAS RN 155860-63-2] (=A1-19);
  nicosulfuron [CAS RN 111991-09-4] (=A1-20);
  sulfosulfuron [CAS RN 141776-32-1] (=A1-28);
  thifensulfuron-methyl [CAS RN 79277-27-3] (=A1-29);
  tribenuron-methyl [CAS RN 101200-48-0] (=A1-31);
  2-iodo-N-[(4-methoxy-6-methyl-1,3,5-triazinyl)carbamoyl]benzene-sulfonamide (=A1-39);
  2-iodo-N-[(4-methoxy-6-methyl-1,3,5-triazinyl)carbamoyl]benzene-sulfonamide sodium salt (=A1-41);
  (A1-83) or its sodium salt (=A1-87);
  propoxycarbazone-sodium [CAS RN 181274-15-7] (=A2-2);
  thiencarbazone-methyl [CAS RN 317815-83-1] (=A2-3);
  florasulam [CAS RN 145701-23-1] (=A3-3);
  metosulam [CAS RN 139528-85-1] (=A3-5);
  pyroxsulam [CAS RN 422556-08-9] (=A3-7)
  (A4-1);
  (A4-2); and
  (A4-3).

ALS inhibitor herbicides which are especially preferably used for control of unwanted vegetation in *Beta vulgaris* (preferably sugar beet) growing areas in which the *Beta vulgaris* (preferably sugar beet) plants contain an ALS protein encoded by an endogenous ALS gene comprising an amino acid different from tryptophan at position 569 and thereby providing tolerance against the ALS inhibitor herbicide(s) according to this invention belonging to group (A) are:
  amidosulfuron [CAS RN 120923-37-7] (=A1-1);
  foramsulfuron [CAS RN 173159-57-4] (=A1-13);
  iodosulfuron-methyl-sodium [CAS RN 144550-36-7] (=A1-16);
  2-iodo-N-[(4-methoxy-6-methyl-1,3,5-triazinyl)carbamoyl]benzene-sulfonamide (=A1-39);

2-iodo-N-[(4-methoxy-6-methyl-1,3,5-triazinyl)carbamoyl]benzene-sulfonamide sodium salt A1-41;

A1-83 or its sodium salt (=A1-87);

thiencarbazone-methyl [CAS RN 317815-83-1] (=A2-3).

Another ALS inhibitor herbicide which is preferably used for control of unwanted vegetation in *Beta vulgaris* (preferably sugar beet) growing areas in which the *Beta vulgaris* (preferably sugar beet) plants contain an ALS protein encoded by an endogenous ALS gene comprising an amino acid different from tryptophan at position 569 and thereby providing tolerance against the ALS inhibitor herbicide(s) according to this invention belonging to group (B) is:

imazamox [CAS RN 114311-32-9] (=B1-2).

Another ALS inhibitor herbicide which is preferably used for control of unwanted vegetation in *Beta vulgaris* (preferably sugar beet) growing areas in which the *Beta vulgaris* (preferably sugar beet) plants contain an ALS protein encoded by an endogenous ALS gene comprising an amino acid different from tryptophan at position 569 and thereby providing tolerance against the ALS inhibitor herbicide(s) according to this invention belonging to group (C) is:

bispyribac-sodium [CAS RN 125401-92-5] (=C1-1).

It is to be further understood that concerning all above defined ALS inhibitor herbicides and where not already specified by the respective CAS RN, all use forms, such as acids, and salts can be applied according to the invention.

Additionally, the ALS inhibitor herbicide(s) to be used according to the invention may comprise further components, for example agrochemically active compounds of a different type of mode of action and/or the formulation auxiliaries and/or additives customary in crop protection, or may be used together with these.

In a preferred embodiment, the herbicide combinations to be used according to the invention comprise effective amounts of the ALS inhibitor herbicide(s) belonging to groups (A), (B) and/or (C) and/or have synergistic actions. The synergistic actions can be observed, for example, when applying one or more ALS inhibitor herbicide(s) belonging to groups (A), (B), and/or (C) together, for example as a coformulation or as a tank mix; however, they can also be observed when the active compounds are applied at different times (splitting). It is also possible to apply the herbicides or the herbicide combinations in a plurality of portions (sequential application), for example pre-emergence applications followed by post-emergence applications or early post-emergence applications followed by medium or late post-emergence applications.

Preference is given here to the joint or almost simultaneous application of the ALS-inhibitor herbicides belonging to groups (A), (B) and/or (C) of the combination in question.

The synergistic effects permit a reduction of the application rates of the individual ALS inhibitor herbicides, a higher efficacy at the same application rate, the control of species which were as yet uncontrolled (gaps), control of species which are tolerant or resistant to individual ALS inhibitor herbicides or to a number of ALS inhibitor herbicides, an extension of the period of application and/or a reduction in the number of individual applications required and—as a result for the user—weed control systems which are more advantageous economically and ecologically.

The herbicides to be used according to this invention are all acetolactate synthase (ALS) inhibitor herbicides (which might alternatively and interchangeably also be named as "ALS inhibiting herbicides") and thus inhibit protein biosynthesis in plants. The application rate of the ALS inhibitor herbicides belonging to groups (A), (B) or (C) (as defined above) can vary within a wide range, for example between 0.001 g and 1500 g of ai/ha (ai/ha means here and below "active substance per hectare"=based on 100% pure active compound). Applied at application rates of from 0.001 g to 1500 g of ai/ha, the herbicides belonging to classes A, B and C according to this invention, preferably the compounds A1-1; A1-4; A1-8; A1-9; A1-12; A1-13; A1-16; A1-17; A1-18; A1-19; A1-20; A1-28; A1-29; A1-31; A1-39; A1-41; A1-83; A1-87; A2-2; A2-3; A3-3; A3-5; A3-7, A4-3, control, when used by the pre- and post-emergence method, a relatively wide spectrum of harmful plants, for example of annual and perennial mono- or dicotyledonous weeds, and also of unwanted crop plants (together also defined as "unwanted vegetation).

In many applications according to the invention, the application rates are generally lower, for example in the range of from 0.001 g to 1000 g of ai/ha, preferably from 0.1 g to 500 g of ai/ha, particularly preferably from 0.5 g to 250 g of ai/ha, and even more preferably 1.0 g to 200 g of ai/ha. In cases where the application of several ALS inhibitor herbicides is conducted, the quantity represents the total quantity of all of the applied ALS inhibitor herbicides.

For example, the combinations according to the invention of ALS inhibitor herbicides (belonging to groups (A), (B) and/or (C)) allow the activity to be enhanced synergistically in a manner which, by far and in an unexpected manner, exceeds the activities which can be achieved using the individual ALS inhibitor herbicides (belonging to groups (A), (B) and/or (C)).

For combinations of ALS inhibitor herbicides, the preferred conditions are illustrated below.

Of particular interest according to present invention is the use of herbicidal compositions for control of unwanted vegetation in *Beta vulgaris* plants, preferably in sugar beet plants having a content of the following ALS inhibitor herbicides:

(A1-1)+(A1-4); (A1-1)+(A1-8); (A1-1)+(A1-9); (A1-1)+(A1-12);

(A1-1)+(A1-13); (A1-1)+(A1-16); (A1-1)+(A1-17); (A1-1)+(A1-18);

(A1-1)+(A1-19); (A1-1)+(A1-20); (A1-1)+(A1-28); (A1-1)+(A1-29);

(A1-1)+(A1-31); (A1-1)+(A1-39); (A1-1)+(A1-41); (A1-1)+(A1-83);

(A1-1)+(A1-87); (A1-1)+(A2-2); (A1-1)+(A2-3); (A1-1)+(A3-3);

(A1-1)+(A3-5); (A1-1)+(A3-7); (A1-1)+(A4-1); (A1-1)+(A4-2); (A1-1)+(A4-3);

(A1-4)+(A1-8); (A1-4)+(A1-9); (A1-4)+(A1-12); (A1-4)+(A1-13);

(A1-4)+(A1-16); (A1-4)+(A1-17); (A1-4)+(A1-18); (A1-4)+(A1-19);

(A1-4)+(A1-20); (A1-4)+(A1-28); (A1-4)+(A1-29); (A1-4)+(A1-31);

(A1-4)+(A1-39); (A1-4)+(A1-41); (A1-4)+(A1-83); (A1-4)+(A1-87);

(A1-4)+(A2-2); (A1-4)+(A2-3); (A1-4)+(A3-3); (A1-4)+(A3-5);

(A1-4)+(A3-7); (A1-4)+(A4-1); (A1-4)+(A4-2); (A1-4)+(A4-3);

(A1-8)+(A1-9); (A1-8)+(A1-12); (A1-8)+(A1-13); (A1-8)+(A1-16);

(A1-8)+(A1-17); (A1-8)+(A1-18); (A1-8)+(A1-19); (A1-8)+(A1-20);

(A1-8)+(A1-28); (A1-8)+(A1-29); (A1-8)+(A1-31); (A1-8)+(A1-39);

(A1-8)+(A1-41); (A1-8)+(A1-83); (A1-8)+(A1-87); (A1-8)+(A2-2);

(A1-8)+(A2-3); (A1-8)+(A3-3); (A1-8)+(A3-5); (A1-8)+(A3-7);
(A1-8)+(A4-1); (A1-8)+(A4-2); (A1-8)+(A4-3);
(A1-9)+(A1-12); (A1-9)+(A1-13); (A1-9)+(A1-16); (A1-9)+(A1-17);
(A1-9)+(A1-18); (A1-9)+(A1-19); (A1-9)+(A1-20); (A1-9)+(A1-28);
(A1-9)+(A1-29); (A1-9)+(A1-31); (A1-9)+(A1-39); (A1-9)+(A1-41);
(A1-9)+(A1-83); (A1-9)+(A1-87); (A1-9)+(A2-2); (A1-9)+(A2-3);
(A1-9)+(A3-3); (A1-9)+(A3-5); (A1-9)+(A3-7); (A1-9)+(A4-1);
(A1-9)+(A4-2); (A1-9)+(A4-3);
(A1-12)+(A1-13); (A1-12)+(A1-16); (A1-12)+(A1-17); (A1-12)+(A1-18);
(A1-12)+(A1-19); (A1-12)+(A1-20); (A1-12)+(A1-28); (A1-12)+(A1-29);
(A1-12)+(A1-31); (A1-12)+(A1-39); (A1-12)+(A1-41); (A1-12)+(A1-83);
(A1-12)+(A1-87); (A1-12)+(A2-2); (A1-12)+(A2-3); (A1-12)+(A3-3);
(A1-12)+(A3-5); (A1-12)+(A3-7); (A1-12)+(A4-1); (A1-12)+(A4-2); (A1-12)+(A4-3);
(A1-13)+(A1-16); (A1-13)+(A1-17); (A1-13)+(A1-18); (A1-13)+(A1-19);
(A1-13)+(A1-20); (A1-13)+(A1-28); (A1-13)+(A1-29); (A1-13)+(A1-31);
(A1-13)+(A1-39); (A1-13)+(A1-41); (A1-13)+(A1-83); (A1-13)+(A1-87);
(A1-13)+(A2-2); (A1-13)+(A2-3); (A1-13)+(A3-3); (A1-13)+(A3-5);
(A1-13)+(A3-7); (A1-13)+(A4-1); (A1-13)+(A4-2); (A1-13)+(A4-3);
(A1-16)+(A1-17); (A1-16)+(A1-18); (A1-16)+(A1-19); (A1-16)+(A1-20);
(A1-16)+(A1-28); (A1-16)+(A1-29); (A1-16)+(A1-31); (A1-16)+(A1-39);
(A1-16)+(A1-41); (A1-16)+(A1-83); (A1-16)+(A1-87); (A1-16)+(A2-2);
(A1-16)+(A2-3); (A1-16)+(A3-3); (A1-16)+(A3-5); (A1-16)+(A3-7);
(A1-16)+(A4-1); (A1-16)+(A4-2); (A1-16)+(A4-3);
(A1-17)+(A1-18); (A1-17)+(A1-19); (A1-17)+(A1-20); (A1-17)+(A1-28);
(A1-17)+(A1-29); (A1-17)+(A1-31); (A1-17)+(A1-39); (A1-17)+(A1-41);
(A1-17)+(A1-83); (A1-17)+(A1-87); (A1-17)+(A2-2); (A1-17)+(A2-3);
(A1-17)+(A3-3); (A1-17)+(A3-5); (A1-17)+(A3-7); (A1-17)+(A4-1);
(A1-17)+(A4-2); (A1-17)+(A4-3);
(A1-18)+(A1-19); (A1-18)+(A1-20); (A1-18)+(A1-28); (A1-18)+(A1-29);
(A1-18)+(A1-31); (A1-18)+(A1-39); (A1-18)+(A1-41); (A1-18)+(A1-83);
(A1-18)+(A1-87); (A1-18)+(A2-2); (A1-18)+(A2-3); (A1-18)+(A3-3);
(A1-18)+(A3-5); (A1-18)+(A3-7); (A1-18)+(A4-1); (A1-18)+(A4-2);
(A1-18)+(A4-3);
(A1-19)+(A1-20); (A1-19)+(A1-28); (A1-19)+(A1-29); (A1-19)+(A1-31);
(A1-19)+(A1-39); (A1-19)+(A1-41); (A1-19)+(A1-83); (A1-19)+(A1-87);
(A1-19)+(A2-2); (A1-19)+(A2-3); (A1-19)+(A3-3); (A1-19)+(A3-5);
(A1-19)+(A3-7); (A1-19)+(A4-1); (A1-19)+(A4-2); (A1-19)+(A4-3);
(A1-20)+(A1-28); (A1-20)+(A1-29); (A1-20)+(A1-31); (A1-20)+(A1-39);
(A1-20)+(A1-41); (A1-20)+(A1-83); (A1-20)+(A1-87); (A1-20)+(A2-2);
(A1-20)+(A2-3); (A1-20)+(A3-3); (A1-20)+(A3-5); (A1-20)+(A3-7);
(A1-20)+(A4-1); (A1-20)+(A4-2); (A1-20)+(A4-3);
(A1-28)+(A1-29); (A1-28)+(A1-31); (A1-28)+(A1-39); (A1-28)+(A1-41);
(A1-28)+(A1-83); (A1-28)+(A1-87); (A1-28)+(A2-2); (A1-28)+(A2-3);
(A1-28)+(A3-3); (A1-28)+(A3-5); (A1-28)+(A3-7); (A1-28)+(A4-1);
(A1-28)+(A4-2); (A1-28)+(A4-3);
(A1-29)+(A1-31); (A1-29)+(A1-39); (A1-29)+(A1-41); (A1-29)+(A1-83);
(A1-29)+(A1-87); (A1-29)+(A2-2); (A1-29)+(A2-3); (A1-29)+(A3-3);
(A1-29)+(A3-5); (A1-29)+(A3-7); (A1-29)+(A4-1); (A1-29)+(A4-2); (A1-29)+(A4-3);
(A1-31)+(A1-39); (A1-31)+(A1-41); (A1-31)+(A1-83); (A1-31)+(A1-87);
(A1-31)+(A2-2); (A1-31)+(A2-3); (A1-31)+(A3-3); (A1-31)+(A3-5);
(A1-31)+(A3-7); (A1-31)+(A4-1); (A1-31)+(A4-2); (A1-31)+(A4-3);
(A1-39)+(A1-41); (A1-39)+(A1-83); (A1-39)+(A1-87); (A1-39)+(A2-2);
(A1-39)+(A2-3); (A1-39)+(A3-3); (A1-39)+(A3-5); (A1-39)+(A3-7);
(A1-39)+(A4-1); (A1-39)+(A4-2); (A1-39)+(A4-3);
(A1-41)+(A1-83); (A1-41)+(A1-87); (A1-41)+(A2-2); (A1-41)+(A2-3);
(A1-41)+(A3-3); (A1-41)+(A3-5); (A1-41)+(A3-7); (A1-41)+(A4-1);
(A1-41)+(A4-2); (A1-41)+(A4-3);
(A1-83)+(A2-2); (A1-83)+(A2-3); (A1-83)+(A3-3); (A1-83)+(A3-5);
(A1-83)+(A3-7); (A1-83)+(A4-1); (A1-83)+(A4-2); (A1-83)+(A4-3);
(A1-87)+(A2-2); (A1-87)+(A2-3); (A1-87)+(A3-3); (A1-87)+(A3-5);
(A1-87)+(A3-7); (A1-87)+(A4-1); (A1-87)+(A4-2); (A1-87)+(A4-3);
(A2-2)+(A2-3); (A2-2)+(A3-3); (A2-2)+(A3-5); (A2-2)+(A3-7);
(A2-2)+(A4-1); (A2-2)+(A4-2); (A2-2)+(A4-3);
(A2-3)+(A3-3); (A2-3)+(A3-5); (A2-3)+(A3-7);
(A2-3)+(A4-1); (A2-3)+(A4-2); (A2-3)+(A4-3);
(A3-3)+(A3-5); (A3-3)+(A3-7);
(A3-3)+(A4-1); (A3-3)+(A4-2); (A3-3)+(A4-3);
(A3-5)+(A3-7); (A3-5)+(A4-1); (A3-5)+(A4-2); (A3-5)+(A4-3);
(A3-7)+(A4-1); (A3-7)+(A4-2); (A3-7)+(A4-3);
(A-1)+(A4-2); (A4-1)+(A4-3); and
(A4-2)+(A4-3);

Additionally, the ALS inhibitor herbicides to be used according to the invention may comprise further components, for example agrochemically active compounds of a different type of mode of action and/or the formulation auxiliaries and/or additives customary in crop protection, or may be used together with these.

The ALS inhibitor herbicide(s) to be used according to the invention or combinations of various such ALS inhibitor herbicides may furthermore comprise various agrochemically active compounds, for example from the group of the safeners, fungicides, insecticides, or from the group of the formulation auxiliaries and additives customary in crop protection.

In a further embodiment, the invention relates to the use of effective amounts of ALS inhibitor herbicide(s) (i.e. members of the groups (A), (B) and/or (C)) and non-ALS inhibitor herbicides (i.e. herbicides showing a mode of action that is different to the inhibition of the ALS enzyme [acetohydroxyacid synthase; EC 2.2.1.6] (group D herbicides) in order obtain synergistic effect for the control of unwanted vegetation. Such synergistic actions can be observed, for example, when applying one or more ALS inhibitor herbicides (i.e. members of the groups (A), (B), and/or (C)) and one or more non-ALS inhibitor herbicides (group D herbicides) together, for example as a coformulation or as a tank mix; however, they can also be observed when the active compounds are applied at different times (splitting). It is also possible to apply the ALS inhibitor herbicides and non-ALS inhibitor herbicides in a plurality of portions (sequential application), for example pre-emergence applications followed by post-emergence applications or early post-emergence applications followed by medium or late post-emergence applications. Preference is given here to the joint or almost simultaneous application of the herbicides ((A), (B) and/or (C)) and (D) of the combination in question.

Suitable partner herbicides to be applied together with ALS inhibitor herbicides are, for example, the following herbicides which differ structurally from the herbicides belonging to the groups (A), (B), and (C) as defined above, preferably herbicidally active compounds whose action is based on inhibition of, for example, acetyl coenzyme A carboxylase, PS I, PS II, HPPDO, phytoene desaturase, protoporphyrinogen oxidase, glutamine synthetase, cellulose biosynthesis, 5-enolpyruvylshikimate 3-phosphate synthetase, as described, for example, in Weed Research 26, 441-445 (1986), or "The Pesticide Manual", 14th edition, The British Crop Protection Council, 2007, or $15^{th}$ edition 2010, or in the corresponding "e-Pesticide Manual", Version 5 (2010), in each case published by the British Crop Protection Council, (hereinbelow in short also "PM"), and in the literature cited therein. Lists of common names are also available in "The Compendium of Pesticide Common Names" on the internet. Herbicides known from the literature (in brackets behind the common name hereinafter also classified by the indicators D1 to D426), which can be combined with ALS-inhibitor herbicides of groups (A), (B) and/or (C) and to be used according to present invention are, for example, the active compounds listed below: (note: the herbicides are referred to either by the "common name" in accordance with the International Organization for Standardization (ISO) or by the chemical name, together where appropriate with a customary code number, and in each case include all use forms, such as acids, salts, esters and isomers, such as stereoisomers and optical isomers, in particular the commercial form or the commercial forms, unless the context indicates otherwise. The citation given is of one use form and in some cases of two or more use forms): acetochlor (=D1), acibenzolar (=D2), acibenzolar-5-methyl (=D3), acifluorfen (=D4), acifluorfen-sodium (=D5), aclonifen (=D6), alachlor (=D7), allidochlor (=D8), alloxydim (=D9), alloxydim-sodium (=D10), ametryn (=D11), amicarbazone (=D12), amidochlor (=D13), aminocyclopyrachlor (=D14), aminopyralid (=D15), amitrole (=D16), ammonium sulfamate (=D17), ancymidol (=D18), anilofos (=D19), asulam (=D20), atrazine (=D21), azafenidin (=D22), aziprotryn (=D23), beflubutamid (=D24), benazolin (=D25), benazolin-ethyl (=D26), bencarbazone (=D27), benfluralin (=D28), benfuresate (=D29), bensulide (=D30), bentazone (=D31), benzfendizone (=D32), benzobicyclon (=D33), benzofenap (=D34), benzofluor (=D35), benzoylprop (=D36), bicyclopyrone (=D37), bifenox (=D38), bilanafos (=D39), bilanafos-sodium (=D40), bromacil (=D41), bromobutide (=D42), bromofenoxim (=D43), bromoxynil (=D44), bromuron (=D45), buminafos (=D46), busoxinone (=D47), butachlor (=D48), butafenacil (=D49), butamifos (=D50), butenachlor (=D51), butralin (=D52), butroxydim (=D53), butylate (=D54), cafenstrole (=D55), carbetamide (=D56), carfentrazone (=D57), carfentrazone-ethyl (=D58), chlomethoxyfen (=D59), chloramben (=D60), chlorazifop (=D61), chlorazifop-butyl (=D62), chlorbromuron (=D63), chlorbufam (=D64), chlorfenac (=D65), chlorfenac-sodium (=D66), chlorfenprop (=D67), chlorflurenol (=D68), chlorflurenol-methyl (=D69), chloridazon (=D70), chlormequat-chloride (=D71), chlornitrofen (=D72), chlorophthalim (=D73), chlorthal-dimethyl (=D74), chlorotoluron (=D75), cinidon (=D76), cinidon-ethyl (=D77), cinmethylin (=D78), clethodim (=D79), clodinafop (=D80), clodinafop-propargyl (=D81), clofencet (=D82), clomazone (=D83), clomeprop (=D84), cloprop (=D85), clopyralid (=D86), cloransulam (=D87), cloransulam-methyl (=D88), cumyluron (=D89), cyanamide (=D90), cyanazine (=D91), cyclanilide (=D92), cycloate (=D93), cycloxydim (=D94), cycluron (=D95), cyhalofop (=D96), cyhalofop-butyl (=D97), cyperquat (=D98), cyprazine (=D99), cyprazole (=D100), 2,4-D (=D101), 2,4-DB (=D102), daimuron/dymron (=D103), dalapon (=D104), daminozide (=D105), dazomet (=D106), n-decanol (=D-107), desmedipham (=D108), desmetryn (=D109), detosyl-pyrazolate (=D110), diallate (=D111), dicamba (=D112), dichlobenil (=D113), dichlorprop (=D114), dichlorprop-P (=D115), diclofop (=D116), diclofop-methyl (=D117), diclofop-P-methyl (=D118), diethatyl (=D119), diethatyl-ethyl (=D120), difenoxuron (=D121), difenzoquat (=D122), diflufenican (=D123), diflufenzopyr (=D124), diflufenzopyr-sodium (=D125), dimefuron (=D126), dikegulac-sodium (=D127), dimefuron (=D128), dimepiperate (=D129), dimethachlor (=D130), dimethametryn (=D131), dimethenamid (=D132), dimethenamid-P (=D133), dimethipin (=D134), dimetrasulfuron (=D135), dinitramine (=D136), dinoseb (=D137), dinoterb (=D138), diphenamid (=D139), dipropetryn (=D140), diquat (=D141), diquat-dibromide (=D142), dithiopyr (=D143), diuron (=D144), DNOC (=D145), eglinazine-ethyl (=D146), endothal (=D147), EPTC (=D148), esprocarb (=D149), ethalfluralin (=D150), ethephon (=D151), ethidimuron (=D152), ethiozin (=D153), ethofumesate (=D154), ethoxyfen (=D155), ethoxyfen-ethyl (=D156), etobenzanid (=D157), F-5331 (=2-Chlor-4-fluor-5-[4-(3-fluorpropyl)-4,5-dihydro-5-oxo-1H-tetrazol-1-yl]-phenyl]-ethansulfonamid) (=D158), F-7967 (=3-[7-Chlor-5-fluor-2-(trifluormethyl)-1H-benzimidazol-4-yl]-1-methyl-6-(trifluormethyl) pyrimidin-2,4(1H,3H)-dion) (=D159), fenoprop (=D160), fenoxaprop (=D161), fenoxaprop-P (=D162), fenoxaprop-ethyl (=D163), fenoxaprop-P-ethyl (=D164), fenoxasulfone (=D165), fentrazamide (=D166), fenuron (=D167), flamprop (=D168), flamprop-M-isopropyl (=D169), flamprop-M-methyl (=D170), fluazifop (=D171), fluazifop-P (=D172), fluazifop-butyl (=D173), fluazifop-P-butyl (=D174), fluazolate (=D175), fluchloralin (=D176), flufenacet (thiafluamide) (=D177), flufenpyr (=D178), flufenpyr-ethyl (=D179), flumetralin (=D180), flumiclorac (=D181), flumiclorac-pentyl (=D182), flumioxazin (=D183), flumipropyn (=D184), fluometuron (=D185), fluorodifen (=D186), fluoroglycofen (=D187), fluoroglycofen-ethyl (=D188), flupoxam (=D189), fluropacil (=D190), flupropanate (=D191), flurenol (=D192), flurenol-butyl (=D193), fluridone (=D194), fluorochloridone (=D195), fluoroxypyr (=D196), fluoroxypyr-meptyl (=D197), flurprimidol (=D198), flurtamone (=D199), fluthiacet (=D200), fluthiacet-methyl (=D201), fluthiamide (=D202), fomesafen (=203), forchlorfenuron (=D204), fosamine (=D205), furyloxyfen (=D206), gibberellic acid (=D207), glufosinate (=D208), glufosinate-ammonium (=D209), glufosinate-P (=D210), glufosinate-P-ammonium (=D211), glufosinate-P-sodium (=D212), glyphosate (=D213), glyphosate-isopropylammonium (=D214), H-9201 (=O-(2,4-Dimethyl-6-nitrophenyl)-O-ethyl-isopropylphosphoramidothioat) (=D215), halosafen (=D216), haloxyfop (=D217), haloxyfop-P (=D218), haloxyfop-ethoxyethyl (=D219), haloxyfop-P-ethoxyethyl (=D220), haloxyfop-methyl (=D221), haloxyfop-P-methyl (=D222), hexazinone (=D223), HW-02 (=1-(Dimethoxyphosphoryl)-ethyl(2,4-dichlorphenoxy)acetate) (=D224), inabenfide (=D225), indanofan (=D226), indaziflam (=D227), indol-3-acetic acid (IAA) (=D228), 4-indol-3-ylbutyric acid (IBA) (=D229), ioxynil (=D230), ipfencarbazone (=D231), isocarbamid (=D232), isopropalin (=D233), isoproturon (=D234), isouron (=D235), isoxaben (=D236), isoxachlortole (=D237), isoxaflutole (=D238), isoxapyrifop (=D239), KUH-043 (=3-({[5-(Difluormethyl)-1-methyl-3-(trifluormethyl)-1H-pyrazol-4-yl]methyl}sulfonyl)-5,5-dimethyl-4,5-dihydro-1,2-oxazol) (=D240), karbutilate (=D241), ketospiradox (=D242), lactofen (=D243), lenacil (=D244), linuron (=D245), male is hydrazide (=D246), MCPA (=D247), MCPB (=D248), MCPB-methyl, -ethyl and -sodium (=D249), mecoprop (=D250), mecoprop-sodium (=D251), mecoprop-butotyl (=D252), mecoprop-P-butotyl (=D253), mecoprop-P-dimethylammonium (=D254), mecoprop-P-2-ethylhexyl (=D255), mecoprop-P-potassium (=D256), mefenacet (=D257), mefluidide (=D258), mepiquat-chloride (=D259), mesotrione (=D260), methabenzthiazuron (=D261), metam (=D262), metamifop (=D263), metamitron (=D264), metazachlor (=D265), metazole (=D266), methiopyrsulfuron (=D267), methiozolin (=D268), methoxyphenone (=D269), methyldymron (=D270), 1-methylcyclopropen (=D271), methylisothiocyanat (=D272), metobenzuron (=D273), metobromuron (=D274), metolachlor (=D275), S-metolachlor (=D-276), metoxuron (=D277), metribuzin (=D278), molinate (=D279), monalide (=D280), monocarbamide (=D281), monocarbamide-dihydrogensulfate (=D282), monolinuron (=D283), monosulfuron-ester (=D284), monuron (=D285), MT-128 (=6-Chlor-N-[(2E)-3-chlorprop-2-en-1-yl]-5-methyl-N-phenylpyridazin-3-amine) (=D286), MT-5950 (=N-[3-Chlor-4-(1-methylethyl)-phenyl]-2-methylpentanamide) (=D287), NGGC-011 (=D288), naproanilide (=D289), napropamide (=D290), naptalam (=D291), NC-310 (=4-(2,4-Dichlorobenzoyl)-1-methyl-5-benzyloxypyrazole) (=D292), neburon (=D293), nipyraclofen (=D294), nitralin (=D295), nitrofen (=D296), nitrophenolat-sodium (isomer mixture) (=D297), nitrofluorfen (=D298), nonanoic acid (=D299), norflurazon (=D300), orbencarb (=D301), oryzalin (=D302), oxadiargyl (=D303), oxadiazon (=D304), oxaziclomefone (=D305), oxyfluorfen (=D306), paclobutrazol (=D307), paraquat (=D308), paraquat-dichloride (=D309), pelargonic acid (nonanoic acid) (=D310), pendimethalin (=D311), pendralin (=D312), pentanochlor (=D313), pentoxazone (=D314), perfluidone (=D315), pethoxamid (=D316), phenisopham (=D317), phenmedipham (=D319), phenmedipham-ethyl (=D320), picloram (=D321), picolinafen (=D322), pinoxaden (=D323), piperophos (=D324), pirifenop (=D325), pirifenop-butyl (=D326), pretilachlor (=D327), probenazole (=D328), profluazol (=D329), procyazine (=D330), prodiamine (=D331), prifluraline (=D332), profoxydim (=D333), prohexadione (=D334), prohexadione-calcium (=D335), prohydrojasmone (=D336), prometon (=D337), prometryn (=D338), propachlor (=D339), propanil (=D340), propaquizafop (=D341), propazine (=D342), propham (=D343), propisochlor (=D344), propyzamide (=D345), prosulfalin (=D346), prosulfocarb (=D347), prynachlor (=D348), pyraclonil (=D349), pyraflufen (=D350), pyraflufen-ethyl (=D351), pyrasulfotole (=D352), pyrazolynate (pyrazolate) (=D353), pyrazoxyfen (=D354), pyribambenz (=D355), pyributicarb (=D356), pyridafol (=D357), pyridate (=D358), pyriminobac (=D359), pyrimisulfan (=D360), pyroxasulfone (=D361), quinclorac (=D362), quinmerac (=D363), quinoclamine (=D364), quizalofop (=D365), quizalofop-ethyl (=D366), quizalofop-P (=D367), quizalofop-P-ethyl (=D368), quizalofop-P-tefuryl (=D369), saflufenacil (=D370), secbumeton (=D371), sethoxydim (=D372), siduron (=D373), simazine (=D374), simetryn (=D375), SN-106279 (=Methyl-(2R)-2-({7-[2-chlor-4-(trifluormethyl)phenoxy]-2-naphthyl}oxy)-propanoate) (=D376), sulcotrione (=D377), sulfallate (CDEC) (=D378), sulfentrazone (=D379), sulfosate (glyphosate-trimesium) (=D380), SYN-523 (=D381), SYP-249 (=1-Ethoxy-3-methyl-1-oxobut-3-en-2-yl-5-[2-chlor-4-(trifluormethyl)phenoxy]-2-nitrobenzoate) (=D382), tebutam (=D383), tebuthiuron (=D384), tecnazene (=D385), tefuryltrione (=D386), tembotrione (=D387), tepraloxydim (=D388), terbacil (=D389), terbucarb (=D390), terbuchlor (=D391), terbumeton (=D392), terbuthylazine (=D393), terbutryn (=D394), thenylchlor (=D395), thiafluamide (=D396), thiazafluoron (=D397), thiazopyr (=D398), thidiazimin (=D399), thidiazuron (=D400), thiobencarb (=D401), tiocarbazil (=D402), topramezone (=D403), tralkoxydim (=D404), triallate (=D405), triaziflam (=D406), triazofenamide (=D407), trichloracetic acid (TCA) (=D408), triclopyr (=D409), tridiphane (=D410), trietazine (=D411), trifluralin (=D412), trimeturon (=D413), trinexapac (=D414), trinexapac-ethyl (=D415), tsitodef (=D416), uniconazole (=D417), uniconazole-P (=D418), vernolate (=D419), ZJ-0862 (=3,4-Dichlor-N-{2-[(4,6-dimethoxypyrimidin-2-yl)oxy]benzyl}aniline) (=D420), and the below compounds defined by their chemical structure, respectively:

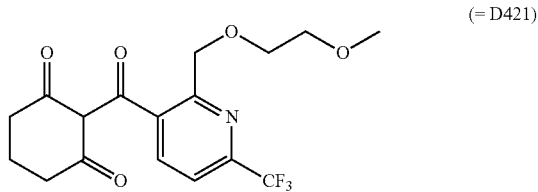

(=D421)

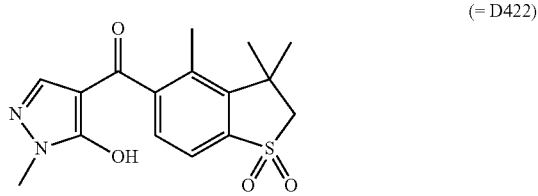

(=D422)

-continued

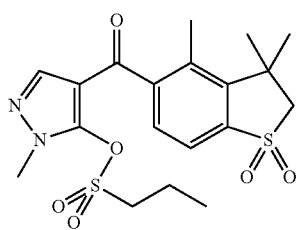 (= D423)

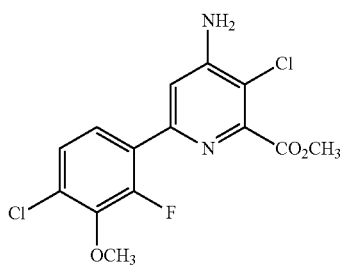 (= D424)

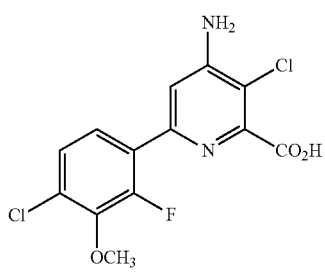 (= D425)

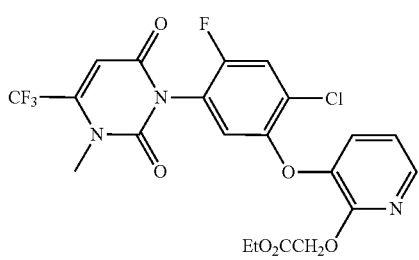 (= D426)

Preferably, further herbicides which differ structurally and via their mode of action from the ALS inhibitor herbicides belonging to the groups (A), (B), and (C) as defined above and to be applied according to the present invention for control of unwanted vegetation in ALS inhibitor herbicide tolerant *Beta vulgaris* plants, preferably sugar beet plants comprising a mutation in codon 1705-1707 of an endogenous ALS gene encoding an ALS protein containing an amino acid that is different from tryptophan at position 569, preferably the tryptophan of the wild-type ALS protein is substituted by a leucine at position 569. In connection with ALS inhibitor herbicides belonging to the groups (A), (B), and (C) are those belonging to the group of:

chloridazon (=D70), clethodim (=D79), clodinafop (=D80), clodinafop-propargyl (=D81), clopyralid (=D86), cycloxydim (=D94), desmedipham (=D108), dimethenamid (=D132), dimethenamid-P (=D133), ethofumesate (=D154), fenoxaprop (=D161), fenoxaprop-P (=D162), fenoxaprop-ethyl (=D163), fenoxaprop-P-ethyl (=D164), fluazifop (=D171), fluazifop-P (=D172), fluazifop-butyl (=D173), fluazifop-P-butyl (=D174), glufosinate (=D208), glufosinate-ammonium (=D209), glufosinate-P (=D210), glufosinate-P-ammonium (=D211), glufosinate-P-sodium (=D212), glyphosate (=D213), glyphosate-isopropylammonium (=D214), haloxyfop (=D217), haloxyfop-P (=D218), haloxyfop-ethoxyethyl (=D219), haloxyfop-P-ethoxyethyl (=D220), haloxyfop-methyl (=D221), haloxyfop-P-methyl (=D222), lenacil (=D244), metamitron (=D264), phenmedipham (=D319), phenmedipham-ethyl (=D320), propaquizafop (=D341), quinmerac (=D363), quizalofop (=D365), quizalofop-ethyl (=D366), quizalofop-P (=D367), quizalofop-P-ethyl (=D368), quizalofop-P-tefuryl (=D369), sethoxydim (=D372), Even more preferably, further herbicides which differ from the ALS inhibitor herbicides belonging to the groups (A), (B), and (C) as defined above and to be applied according to the invention in connection with ALS inhibitor herbicides belonging to the groups (A), (B), and (C) are those belonging to the group of: desmedipham (=D108), ethofumesate (=D154), glufosinate (=D208), glufosinate-ammonium (=D209), glufosinate-P (=D210), glufosinate-P-ammonium (=D211), glufosinate-P-sodium (=D212), glyphosate (=D213), glyphosate-isopropylammonium (=D214), lenacil (=D244), metamitron (=D264), phenmedipham (=D319), phenmedipham-ethyl (=D320).

Mixtures containing ALS inhibitor herbicides and non-ALS inhibitor herbicides, compositions comprising mixtures of one or more ALS inhibitor herbicide(s) (compounds belonging to one or more of groups (A), (B) and (C)) and non-ALS inhibitor heribicide(s) (group (D) members; as defined above) that are of very particular interest in order to be used according to present invention for control of unwanted vegetation are:

(A1-1)+(D108); (A1-1)+(D154); (A1-1)+(D208); (A1-1)+(D209);
(A1-1)+(D210); (A1-1)+(D212); (A1-1)+(D213); (A1-1)+(D214);
(A1-1)+(D244); (A1-1)+(D264); (A1-1)+(D319); (A1-1)+(D320).
(A1-13)+(D108); (A1-13)+(D154); (A1-13)+(D208); (A1-13)+(D209);
(A1-13)+(D210); (A1-13)+(D212); (A1-13)+(D213); (A1-13)+(D214);
(A1-13)+(D244); (A1-13)+(D264); (A1-13)+(D319); (A1-13)+(D320).
(A1-16)+(D108); (A1-16)+(D154); (A1-16)+(D208); (A1-16)+(D209);
(A1-16)+(D210); (A1-16)+(D212); (A1-16)+(D213); (A1-16)+(D214);
(A1-16)+(D244); (A1-16)+(D264); (A1-16)+(D319); (A1-16)+(D320).
(A1-39)+(D108); (A1-39)+(D154); (A1-39)+(D208); (A1-39)+(D209);
(A1-39)+(D210); (A1-39)+(D212); (A1-39)+(D213); (A1-39)+(D214);
(A1-39)+(D244); (A1-39)+(D264); (A1-39)+(D319); (A1-39)+(D320).
(A1-41)+(D108); (A1-41)+(D154); (A1-41)+(D208); (A1-41)+(D209);
(A1-41)+(D210); (A1-41)+(D212); (A1-41)+(D213); (A1-41)+(D214);
(A1-41)+(D244); (A1-41)+(D264); (A1-41)+(D319); (A1-41)+(D320).
(A1-83)+(D108); (A1-83)+(D154); (A1-83)+(D208); (A1-83)+(D209);
(A1-83)+(D210); (A1-83)+(D212); (A1-83)+(D213); (A1-83)+(D214);
(A1-83)+(D244); (A1-83)+(D264); (A1-83)+(D319); (A1-83)+(D320).
(A1-87)+(D108); (A1-87)+(D154); (A1-87)+(D208); (A1-87)+(D209);

(A1-87)+(D210); (A1-87)+(D212); (A1-87)+(D213); (A1-87)+(D214);

(A1-87)+(D244); (A1-87)+(D264); (A1-87)+(D319); (A1-87)+(D320).

(A2-3)+(D108); (A2-3)+(D154); (A2-3)+(D208); (A2-3)+(D209);

(A2-3)+(D210); (A2-3)+(D212); (A2-3)+(D213); (A2-3)+(D214);

(A2-3)+(D244); (A2-3)+(D264); (A2-3)+(D319); (A2-3)+(D320).

(B1-2)+(D108); (B1-2)+(D154); (B1-2)+(D208); (B1-2)+(D209);

(B1-2)+(D210); (B1-2)+(D212); (B1-2)+(D213); (B1-2)+(D214);

(B1-2)+(D244); (B1-2)+(D264); (B1-2)+(D319); (B1-2)+(D320).

(C1-1)+(D108); (C1-1)+(D154); (C1-1)+(D208); (C1-1)+(D209);

(C1-1)+(D210); (C1-1)+(D212); (C1-1)+(D213); (C1-1)+(D214);

(C1-1)+(D244); (C1-1)+(D264); (C1-1)+(D319); (C1-1)+(D320).

The application of ALS inhibitor herbicides also act efficiently on perennial weeds which produce shoots from rhizomes, root stocks and other perennial organs and which are difficult to control. Here, the substances can be applied, for example, by the pre-sowing method, the pre-emergence method or the post-emergence method, for example jointly or separately. Preference is given, for example, to application by the post-emergence method, in particular to the emerged harmful plants.

Specific examples may be mentioned of some representatives of the monocotyledonous and dicotyledonous weed flora which can be controlled by the ALS inhibitor herbicides, without the enumeration being restricted to certain species.

Examples of weed species on which the application according to present invention act efficiently are, from amongst the monocotyledonous weed species, *Avena* spp., *Alopecurus* spp., *Apera* spp., *Brachiaria* spp., *Bromus* spp., *Digitaria* spp., *Lolium* spp., *Echinochloa* spp., *Panicum* spp., *Phalaris* spp., *Poa* spp., *Setaria* spp. and also *Cyperus* species from the annual group, and, among the perennial species, *Agropyron, Cynodon, Imperata* and *Sorghum* and also perennial *Cyperus* species.

In the case of the dicotyledonous weed species, the spectrum of action extends to genera such as, for example, *Abutilon* spp., *Amaranthus* spp., *Chenopodium* spp., *Chrysanthemum* spp., *Galium* spp., *Ipomoea* spp., *Kochia* spp., *Lamium* spp., *Matricaria* spp., *Pharbitis* spp., *Polygonum* spp., *Sida* spp., *Sinapis* spp., *Solanum* spp., *Stellaria* spp., *Veronica* spp. and *Viola* spp., *Xanthium* spp., among the annuals, and *Convolvulus, Cirsium, Rumex* and *Artemisia* in the case of the perennial weeds.

It is preferred that the *Beta vulgaris* plant, preferably sugar beet plant, to which one or more ALS inhibitor herbicide(s) alone or in combination with one or more herbicide(s) that do(es) not belong to the class of ALS inhibitor herbicides are applied for control of unwanted vegetation in *Beta vulgaris*, preferably in sugar beet growing areas in which *Beta vulgaris* plants, preferably sugar beet comprise a mutation in codon 1705-1707 of an endogenous ALS gene encoding an ALS protein containing an amino acid that is different from tryptophan at position 569, is orthoploid or anorthoploid. Herein, an orthoploid plant may preferably be haploid, diploid, tetraploid, hexaploid, octaploid, decaploid or dodecaploid, while an anorthoploid plant may preferably be triploid or pentaploid.

As used herein unless clearly indicated otherwise, the term "plant" intended to mean a plant at any developmental stage.

It might be, that—depending on the respective genetic background—*Beta vulgaris* plants of the same genetic background in which such mutation is only heterozygously present, the herbicide tolerant *Beta vulgaris* plants which are homozygous for the non-transgenic mutation of the endogenous ALS gene reveal a better agronomical level of ALS inhibitor herbicide tolerance.

In this context "homozygous" indicates that a plant of the present invention has two copies of the same allele on different DNA strands, in particular at the ALS gene locus.

Accordingly, when used herein the term "heterozygous" or "heterozygously" means that a plant of the present invention has different alleles at a particular locus, in particular at the ALS gene locus.

Therefore, present invention relates to the use of one or more ALS inhibitor herbicide(s) alone or in combination with one or more non-ALS inhibitor herbicide(s) for weed control in *Beta vulgaris*, preferably in sugar beet growing areas in which the *Beta vulgaris* plants, preferably sugar beet plants comprise a mutation in codon 1705-1707 of an endogenous ALS gene encoding an ALS protein containing an amino acid that is different from tryptophan at position 569, preferably the tryptophan of the wild-type ALS protein is substituted by a leucine at position 569. This respective mutation at position 1705-1707 of the endogeneous ALS gene can be heterozygously present, and can preferably be the sole mutation of the ALS gene. More preferably, the respective mutation can be homozygously present, and most preferably, the respective mutation is homozygously present as the sole mutation of the endogenous ALS gene.

Owing to their herbicidal and plant growth-regulatory properties, ALS inhibitor herbicides belonging to one or more of the groups (A), (B), and (C) either alone or in combination with non-ALS inhibitor herbicides can be employed for controlling harmful plants in known *Beta vulgaris*, preferably sugar beet plants but also in tolerant or genetically modified crop plants that do already exists or need still to be developed. In general, the transgenic plants are distinguished by specific advantageous properties, in addition to tolerances to the ALS inhibitor herbicides according to the invention, for example, by tolerances to non-ALS inhibitor herbicides, resistances to plant diseases or the causative organisms of plant diseases such as certain insects or microorganisms, such as funghi, bacteria or viruses. Other specific characteristics relate, for example, to the harvested material with regard to quantity, quality, storability, composition and specific constituents. Thus, transgenic plants are known whose starch content is increased, or whose starch quality is altered, or those where the harvested material has a different fatty acid composition.

Conventional methods of generating novel plants which have modified properties in comparison to plants occurring to date consist, for example, in traditional breeding methods and the generation of mutants. Alternatively, novel plants with altered properties can be generated with the aid of recombinant methods (see, for example, EP-A-0221044, EP-A-0131624). For example, the following have been described in several cases:

the modification, by recombinant technology, of crop plants with the aim of modifying the starch synthesized in the plants (for example WO 92/11376, WO 92/14827, WO 91/19806), transgenic crop plants which exhibit tolerance to non-ALS inhibitor herbicides, transgenic crop plants with the capability of producing *Bacillus thuringiensis* toxins (Bt toxins), which make the plants resistant to certain pests (EP-A-0142924, EP-A-0193259), transgenic crop plants with a modified fatty acid composition (WO 91/13972).

A large number of techniques in molecular biology are known in principle with the aid of which novel transgenic plants with modified properties can be generated; see, for example, Sambrook et al., 1989, Molecular Cloning, A Laboratory Manual, $2^{nd}$ Edition, Cold Spring Harbor Laboratory Press, Cold Spring Harbor, N.Y.; or Winnacker "Gene and Klone", VCH Weinheim $2^{nd}$ Edition 1996 or Christou, "Trends in Plant Science" 1 (1996) 423-431).

To carry out such recombinant manipulations, nucleic acid molecules which allow mutagenesis or sequence changes by recombination of DNA sequences can be introduced into plasmids. For example, the abovementioned standard methods allow base exchanges to be carried out, subsequences to be removed, or natural or synthetic sequences to be added. To connect the DNA fragments to each other, adapters or linkers may be added to the fragments.

For example, the generation of plant cells with a reduced activity of a gene product can be achieved by expressing at least one corresponding antisense RNA, a sense RNA for achieving a cosuppression effect or by expressing at least one suitably constructed ribozyme which specifically cleaves transcripts of the above-mentioned gene product.

To this end, it is possible to use DNA molecules which encompass the entire coding sequence of a gene product inclusive of any flanking sequences which may be present, and also DNA molecules which only encompass portions of the coding sequence, it being necessary for these portions to be long enough to have an antisense effect in the cells. The use of DNA sequences which have a high degree of homology to the coding sequences of a gene product, but are not completely identical to them, is also possible.

When expressing nucleic acid molecules in plants, the protein synthesized can be localized in any desired compartment of the plant cell. However, to achieve localization in a particular compartment, it is possible, for example, to link the coding region with DNA sequences which ensure localization in a particular compartment. Such sequences are known to those skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106).

The transgenic plant cells can be regenerated by known techniques to give rise to entire plants. Thus, transgenic *Beta vulgaris* plants, preferably sugar beet plants can be obtained whose properties are altered by overexpression, suppression or inhibition of homologous (=natural) genes or gene sequences or the expression of heterologous (=foreign) genes or gene sequences.

The present invention furthermore provides a method for controlling unwanted vegetation in *Beta vulgaris* plants, preferably in sugar beet, which comprises applying one or more ALS inhibitor herbicides belonging to groups (A), (B) and/or (C) to the plants (for example harmful plants, such as monocotyledonous or dicotyledonous weeds or unwanted crop plants), the seed (seeds or vegetative propagation organs, such as tubers or shoot parts) or to the area in which the plants grow (for example the area under cultivation), for example together or separately.

The present invention furthermore provides a method for controlling unwanted vegetation in *Beta vulgaris* plants, preferably in sugar beet, which comprises applying one or more ALS inhibitor herbicide(s) belonging to groups (A), (B) and/or (C) alone or in combination with non-ALS inhibitor herbicides belonging to class (D) compound according to the invention to the plants (for example harmful plants, such as monocotyledonous or dicotyledonous weeds or unwanted crop plants), the seed (seeds or vegetative propagation organs, such as tubers or shoot parts) or to the area in which the plants grow (for example the area under cultivation), for example together or separately. One or more non-ALS inhibitor herbicides may be applied in combination with one or more ALS inhibitor herbicide(s) before, after or simultaneously with the ALS inhibitor herbicide(s) to the plants, the seed or the area in which the plants grow (for example the area under cultivation).

"Unwanted plants" or "unwanted vegetation" are to be understood as meaning all plants which grow in locations where they are unwanted. This can, for example, be harmful plants (for example monocotyledonous or dicotyledonous weeds or unwanted crop plants).

The herbicide combinations to be used according to the invention can be prepared by known processes, for example as mixed formulations of the individual components, if appropriate with further active compounds, additives and/or customary formulation auxiliaries, which combinations are then applied in a customary manner diluted with water, or as tank mixes by joint dilution of the components, formulated separately or formulated partially separately, with water. Also possible is the split application of the separately formulated or partially separately formulated individual components.

It is also possible to apply ALS inhibitor herbicides or the combination comprising ALS inhibitor herbicide(s) and non-ALS inhibitor herbicide(s) in a plurality of portions (sequential application) using, for example, pre-emergence applications followed by post-emergence applications or using early post-emergence applications followed by medium or late post-emergence applications. Preference is given here to the joint or almost simultaneous application of the active compounds of the combination in question.

The herbicides belonging to any of the above defined groups (A), (B), (C) and (D) and to be applied according to present invention can be converted jointly or separately into customary formulations, such as solutions, emulsions suspensions, powders, foams, pastes, granules, aerosols, natural and synthetic materials impregnated with active compound and microencapsulations in polymeric materials. The formulations may comprise the customary auxiliaries and additives.

These formulations are produced in a known manner, for example by mixing the active compounds with extenders, that is liquid solvents, pressurized liquefied gases and/or solid carriers, if appropriate with the use of surfactants, that is emulsifiers and/or dispersants, and/or foam formers.

If the extender used is water, it is also possible to use, for example, organic solvents as auxiliary solvents. Suitable liquid solvents are essentially: aromatics, such as xylene, toluene, alkylnaphthalenes, chlorinated aromatics or chlorinated aliphatic hydrocarbons, such as chlorobenzenes, chloroethylenes, or methylene chloride, aliphatic hydrocarbons, such as cyclohexane or paraffins, for example mineral oil fractions, mineral and vegetable oils, alcohols, such as butanol or glycol, and ethers and esters thereof, ketones, such as acetone, methyl ethyl ketone, methyl isobutyl ketone or cyclohexanone, strongly polar solvents, such as dimethylformamide or dimethyl sulfoxide, and also water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks, such as calcite, marble, pumice, sepiolite and dolomite, and also synthetic granules of inorganic and organic meals, and granules of organic material, such as sawdust, coconut shells, corn cobs and tobacco stalks; suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates and also protein hydrolysates; suitable dispersants are: for example lignosulfite waste liquors and methylcellulose.

Tackifiers such as carboxymethylcellulose and natural and synthetic polymers in the form of powders, granules or latices, such as gum arabic, polyvinyl alcohol and polyvinyl acetate, and also natural phospholipids, such as cephalins and lecithins and synthetic phospholipids, can be used in the formulations. Other possible additives are mineral and vegetable oils.

The herbicidal action of the herbicide combinations to be used according to the invention can be improved, for example, by surfactants, preferably by wetting agents from the group of the fatty alcohol polyglycol ethers. The fatty alcohol polyglycol ethers preferably comprise 10-18 carbon atoms in the fatty alcohol radical and 2-20 ethylene oxide units in the polyglycol ether moiety. The fatty alcohol polyglycol ethers may be present in nonionic form, or ionic form, for example in the form of fatty alcohol polyglycol ether sulfates, which may be used, for example, as alkali metal salts (for example sodium salts and potassium salts) or ammonium salts, or even as alkaline earth metal salts, such as magnesium salts, such as $C_{12}/C_{14}$-fatty alcohol diglycol ether sulfate sodium (Genapol® LRO, Clariant GmbH); see, for example, EP-A-0476555, EP-A-0048436, EP-A-0336151 or U.S. Pat. No. 4,400,196 and also Proc. EWRS Symp. "Factors Affecting Herbicidal Activity and Selectivity", 227-232 (1988). Nonionic fatty alcohol polyglycol ethers are, for example, ($C_{10}$-$C_{18}$)—, preferably ($C_{10}$-$C_{14}$)-fatty alcohol polyglycol ethers (for example isotridecyl alcohol polyglycol ethers) which comprise, for example, 2-20, preferably 3-15, ethylene oxide units, for example those from the Genapol® X-series, such as Genapol® X-030, Genapol® X-060, Genapol® X-080 or Genapol® X-150 (all from Clariant GmbH).

The present invention further comprises the combination of ALS inhibitor herbicides belonging to any of the groups (A), (B), and (C) according to present invention with the wetting agents mentioned above from the group of the fatty alcohol polyglycol ethers which preferably contain 10-18 carbon atoms in the fatty alcohol radical and 2-20 ethylene oxide units in the polyglycol ether moiety and which may be present in nonionic or ionic form (for example as fatty alcohol polyglycol ether sulfates). Preference is given to $C_{12}/C_{14}$-fatty alcohol diglycol ether sulfate sodium (Genapol® LRO, Clariant GmbH) and isotridecyl alcohol polyglycol ether having 3-15 ethylene oxide units, for example from the Genapol® X-series, such as Genapol® X-030, Genapol® X-060, Genapol® X-080 and Genapol® X-150 (all from Clariant GmbH). Furthermore, it is known that fatty alcohol polyglycol ethers, such as nonionic or ionic fatty alcohol polyglycol ethers (for example fatty alcohol polyglycol ether sulfates) are also suitable for use as penetrants and activity enhancers for a number of other herbicides (see, for example, EP-A-0502014).

Furthermore, it is known that fatty alcohol polyglycol ethers, such as nonionic or ionic fatty alcohol polyglycol ethers (for example fatty alcohol polyglycol ether sulfates) are also suitable for use as penetrants and activity enhancers for a number of other herbicides (see, for example, EP-A-0502014).

The herbicidal action of the herbicide combinations according to the invention can also be enhanced by using vegetable oils. The term vegetable oils is to be understood as meaning oils of oleaginous plant species, such as soybean oil, rapeseed oil, corn oil, sunflower oil, cottonseed oil, linseed oil, coconut oil, palm oil, thistle oil or castor oil, in particular rapeseed oil, and also their transesterification products, for example alkyl esters, such as rapeseed oil methyl ester or rapeseed oil ethyl ester.

The vegetable oils are preferably esters of $C_{10}$-$C_{22}$-, preferably $C_{12}$-$C_{20}$-, fatty acids. The $C_{10}$-$C_{22}$-fatty acid esters are, for example, esters of unsaturated or saturated $C_{10}$-$C_{22}$-fatty acids, in particular those having an even number of carbon atoms, for example erucic acid, lauric acid, palmitic acid and in particular $C_{18}$-fatty acids, such as stearic acid, oleic acid, linoleic acid or linolenic acid.

Examples of $C_{10}$-$C_{22}$-fatty acid esters are esters obtained by reacting glycerol or glycol with the $C_{10}$-$C_{22}$-fatty acids contained, for example, in oils of oleaginous plant species, or $C_1$-$C_{20}$-alkyl-$C_{10}$-$C_{22}$-fatty acid esters which can be obtained, for example, by transesterification of the aforementioned glycerol- or glycol-$C_{10}$-$C_{22}$-fatty acid esters with $C_1$-$C_{20}$-alcohols (for example methanol, ethanol, propanol or butanol). The transesterification can be carried out by known methods as described, for example, in Römpp Chemie Lexikon, 9th edition, Volume 2, page 1343, Thieme Verlag Stuttgart.

Preferred $C_1$-$C_{20}$-alkyl-$C_{10}$-$C_{22}$-fatty acid esters are methyl esters, ethyl esters, propyl esters, butyl esters, 2-ethylhexyl esters and dodecyl esters. Preferred glycol- and glycerol-$C_{10}$-$C_{22}$-fatty acid esters are the uniform or mixed glycol esters and glycerol esters of $C_{10}$-$C_{22}$-fatty acids, in particular fatty acids having an even number of carbon atoms, for example erucic acid, lauric acid, palmitic acid and, in particular, $C_{18}$-fatty acids, such as stearic acid, oleic acid, linoleic acid or linolenic acid.

In the herbicidal compositions to be used according to the invention, the vegetable oils can be present, for example, in the form of commercially available oil-containing formulation additives, in particular those based on rapeseed oil, such as Hasten® (Victorian Chemical Company, Australia, hereinbelow referred to as Hasten, main ingredient: rapeseed oil ethyl ester), Actirob®B (Novance, France, hereinbelow referred to as ActirobB, main ingredient: rapeseed oil methyl ester), Rako-Binol® (Bayer AG, Germany, hereinbelow referred to as Rako-Binol, main ingredient: rapeseed oil), Renol® (Stefes, Germany, hereinbelow referred to as Renol, vegetable oil ingredient: rapeseed oil methyl ester) or Stefes Mero® (Stefes, Germany, hereinbelow referred to as Mero, main ingredient: rapeseed oil methyl ester).

In a further embodiment, herbicidal combinations to be used according to present invention can be formulated with the vegetable oils mentioned above, such as rapeseed oil, preferably in the form of commercially available oil-containing formulation additives, in particular those based on rapeseed oil, such as Hasten® (Victorian Chemical Company, Australia, hereinbelow referred to as Hasten, main ingredient: rapeseed oil ethyl ester), Actirob®B (Novance, France, hereinbelow referred to as ActirobB, main ingredient: rapeseed oil methyl ester), Rako-Binol® (Bayer AG, Germany, hereinbelow referred to as Rako-Binol, main ingredient: rapeseed oil), Renol® (Stefes, Germany, hereinbelow referred to as Renol, vegetable oil ingredient: rapeseed oil methyl ester) or Stefes Mero® (Stefes, Germany, hereinbelow referred to as Mero, main ingredient: rapeseed oil methyl ester).

It is possible to use colorants, such as inorganic pigments, for example iron oxide, titanium oxide, Prussian Blue, and organic dyes, such as alizarin dyes, azo dyes and metal phthalocyanine dyes, and trace nutrients such as salts of iron, manganese, boron, copper, cobalt, molybdenum and zinc.

The formulations to be used according to present invention generally comprise from 0.1 to 95% by weight of active compounds, preferably from 0.5 to 90% by weight.

As such or in their formulations, the ALS inhibitor herbicides belonging to any of the above defined groups (A), (B), and (C) can also be used as a mixture with other agrochemically active compounds, such as known non-ALS inhibitor herbicides, for controlling unwanted vegetation, for example for controlling weeds or for controlling unwanted crop plants, finished formulations or tank mixes, for example, being possible.

The use of a mixture of ALS inhibitor herbicides belonging to any of the above defined groups (A), (B), and (C) with other known active compounds, such as fungicides, insecticides, acaricides, nematicides, safeners, bird repellants, plant nutrients and soil structure improvers is likewise possible.

The ALS inhibitor herbicides belonging to any of the above defined groups (A), (B), (C) can be used as such, in the form of their formulations or in the use forms prepared therefrom by further dilution, such as ready-to-use solutions, suspensions, emulsions, powders, pastes and granules. Application is carried out in a customary manner, for example by watering, spraying, atomizing, broadcasting.

According to the invention, one or more of the ALS inhibitor herbicides belonging to any of the above defined groups (A), (B), and (C) can be applied either alone or in combination with one or more non-ALS inhibitor herbicides belonging to group (D) to the plants (for example harmful plants, such as monocotyledonous or dicotyledonous weeds or unwanted crop plants), the seed (for example grains, seeds or vegetative propagation organs, such as tubers or shoot parts with buds) or the area under cultivation (for example the soil), preferably to the green plants and parts of plants and, if appropriate, additionally the soil. One possible use is the joint application of the active compounds in the form of tank mixes, where the optimally formulated concentrated formulations of the individual active compounds are, together, mixed in a tank with water, and the spray liquor obtained is applied.

Biological Examples

Selection for Obtaining ALS Inhibitor Tolerant *Beta vulgaris* Plants

The making, selection and propagation of the respective ALS inhibitor herbicide tolerant *Beta vulgaris* mutants and their progenies that were used in all the biological examples disclosed subsequently is described in detail in the European Patent Application having the title "ALS inhibitor herbicide tolerant *Beta vulgaris* mutants" and which was filed electronically on 15 Oct. 2010 at the European Patent Office, of which Bayer CropScience AG is a co-applicant, and which has received the Application number EP10187751.2, and, further, in the PCT application claiming EP10187751.2 as priority application.

Therefore, these respective techniques concerning the preparation of such ALS inhibitor herbicide tolerant *Beta vulgaris* mutants, esp. sugar beet mutants comprising a mutation at position 569 of the ALS encoded by the endogenous ALS gene are described herein only in brief and the content, especially concerning Examples 1 to 5 of the above cited patent application is referenced in its entirety.

Sugar beet cell cultures were initiated from seedlings of a diploid sugar beet genotype 7T9044 (as, for example, described by Alexander Dovzhenko, PhD Thesis, Title: "Towards plastid transformation in rapeseed (*Brassica napus* L.) and sugarbeet (*Beta vulgaris* L.)", Ludwig-Maximilians-Universität München, Germany, 2001).

Callus obtained therefrom was exposed to $10^{-7}$ M foramsulfuron.

Surviving and growing cell colonies were numbered and transferred after 4-6 weeks onto fresh medium containing $3 \times 10^{-7}$ M of the inhibitor. One of these cell colonies was able to grow not only at this concentration of the inhibitor but even in presence of $3 \times 10^{-6}$ M of foramsulfuron [CAS RN 173159-57-4].

From this clone (SB574TL), shoots were regenerated in presence of the ALS inhibitor herbicide and then the shoots were transferred to MS medium containing 0.05 mg/l Naphthalene acetic acid (NAA).

During the first 10-15 days after transfer into soil containing substrate the plants were kept in an environment with high air humidity. During and after they were weaned to normal greenhouse air humidity regimes the plants were kept in the greenhouse under artificial light (12 h) at 20+−3° C./15+−2° C. day/night temperatures.

3-5 weeks later, the regenerated plants from the above obtained foramsulfuron tolerant cell culture (SB574TL) as well as from the wild type cell cultures were treated with foramsulfuron, iodosulfuron-methyl-sodium (CAS RN 144550-3-7) and a mixture of both active ingredients. The herbicide doses tested were equivalent to 7-70 g a.i./ha for foramsulfuron and 1-10 g a.i./ha for iodosulfuron-methyl-sodium.

Regenerated plants from this tolerant cell line tolerated even the highest herbicide doses (foramsulfuron, iodosulfuron-methyl-sodium and their mixtures in the ratio 7:1) whereas even the lowest doses killed the wild type plants.

The homozygous seedlings tolerated mixtures of 35 g foramsulfuron/ha+7 g iodosulfuron-methyl-sodium/ha without growth retardation or any signs of visible damage. In several cases, heterozygous lines showed signs of retarded growth and some leaf chlorosis at these rates, but they recovered within 3-5 weeks, whereas the conventional sugar beet seedlings were killed by the ALS inhibitor herbicides.

Obtained seeds, containing the tryptophan to leucin mutation at position 569 of the ALS protein encoded by the endogenous sugar beet ALS gene (based on SB574TL) have been deposited with the NCIMB, Aberdeen, UK, under Number NCIMB 41705 with Bayer CropScience AG as a co-depositor.

Attached Sequences (SEQ ID NOs 1 to 4)

Attached SEQ ID No 1 represents the wild-type nucleic acid sequence of sugar beet genotype 7T9044; SEQ ID NO 2 represents the ALS protein encoded by SEQ ID No 1; SEQ ID No 3 represents the obtained mutated ALS gene of the sugar beet mutant line "SB574TL" and SEQ ID No 4 represents the Trp→Leu mutated ALS protein at position 569 which is encoded by the nucleic acid sequence disclosed under SEQ ID No 3 and which is present in the endogenous ALS gene of SB574TL that has been deposited under number NCIMB 41705 at the NCIMB, Aberdeen, UK.

2. Field Trials by Employing Homozygous ALS Inhibitor Herbicide Tolerant Sugar Beet Plants Based on SB574TL, F4-F6 seeds conferring the mutant allele of the endogenous ALS gene in the homozygous state were applied for further testing.

Plant seeds of the homozygous SB574TL mutant plants and those of the traditional varieties KLARINA and BERETTA (both commonly available ALS inhibitor sensitive reference sugar beet varieties, not having the respective mutation at position 569 in the ALS protein.) were sown in the field and grew up to various growth stages according to the BBCH standard (as defined in the monographie "Entwicklungsstadien mono-und dikotyler Pflanzen", 2nd edition, 2001, ed. Uwe Meier, Biologische Bundesanstalt für Land und Forstwirtschaft).

Afterwards the plants were treated with the respective ALS inhibitor herbicides as specified in Tables 1, 2 and 3, below.

The water quantity applied in the various applications equaled 200 l/ha.

At 8, 14, 16, 17, 28, and 31 days (as indicated in the various Tables) after application (DAA) of the respective ALS inhibitor herbicide(s), the damages (phytotoxicity/phyto) on the different sugar beet plants were scored according to the scale from 0% to 100%.

In this context, "0%" means "no phytotoxicity/phyto" and "100%" means plants were completely killed.

The obtained results are given in detail in Tables 1, 2, and 3, below.

TABLE 1

| | | SB574TL based sugar beet | | | KLARINA | | |
|---|---|---|---|---|---|---|---|
| | | Stage of application | | | | | |
| | | BBCH 14 | BBCH 14 | BBCH 14 | BBCH 14 | BBCH 14 | BBCH 14 |
| | | | | Rating | | | |
| | | % phyto | % phyto | % phyto | % phyto | % phyto | % phyto |
| | | Application - Assessment interval | | | | | |
| Active substance | gai/ha | 8 DAA | 17 DAA | 31 DAA | 8 DAA | 17 DAA | 31 DAA |
| Foramsulfuron (A1-13) + | 25 | 0 | 0 | 0 | 83 | 95 | 100 |
| Thiencarbazone-methyl (A2-3) | 15 | | | | | | |
| Foramsulfuron (A1-13) + | 50 | 0 | 0 | 0 | 85 | 98 | 100 |
| Thiencarbazone-methyl (A2-3) | 30 | | | | | | |
| Compound (A1-87) | 30 | 0 | 0 | 0 | 83 | 100 | 100 |
| Iodosulfuron-methyl-sodium (A1-16) | 15 | 0 | 0 | 0 | 83 | 98 | 100 |

According to the data disclosed in Table 1, it can clearly be demonstrated that SB574TL based sugar beet plants are fully tolerant to the application of various ALS inhibitor herbicides, i.e. in single application of one ALS inhibitor herbicide but also in a combined application of 2 different ALS inhibitor herbicides (foramsulfuron+thencarbacone-methyl) belonging to 2 different subgroups ((A1) and (A2)) of group (A), i.e. (sulfon)amides whereas the conventional variety KLARINA is significantly damaged under identical growing conditions.

TABLE 2

| | | Variety characteristic | | | | | |
|---|---|---|---|---|---|---|---|
| | | KLARINA | SB574TL based sugar beet | KLARINA | SB574TL based sugar beet | KLARINA | SB574TL based sugar beet |
| | | Stage of application | | | | | |
| | | BBCH 14 | BBCH 14 | BBCH 14 | BBCH 14 | BBCH 14 | BBCH 14 |
| | | | | Rating | | | |
| | | % phyto | % phyto | % phyto | % phyto | % phyto | % phyto |
| | | Application - Assessment interval | | | | | |
| Active substance | gai/ha | 8 days | 8 days | 14 days | 14 days | 28 days | 28 days |
| Foramsulfuron (A1-13) | 25 g/ha | 85 | 0 | 83 | 0 | 86 | 0 |
| Foramsulfuron (A1-13) | 50 g/ha | 90 | 0 | 92 | 0 | 94 | 0 |

TABLE 2-continued

| | | Variety characteristic | | | | | |
|---|---|---|---|---|---|---|---|
| | | KLARINA | SB574TL based sugar beet | KLARINA | SB574TL based sugar beet | KLARINA | SB574TL based sugar beet |
| | | Stage of application | | | | | |
| | | BBCH 14 | BBCH 14 | BBCH 14 | BBCH 14 | BBCH 14 | BBCH 14 |
| | | Rating | | | | | |
| | | % phyto | % phyto | % phyto | % phyto | % phyto | % phyto |
| | | Application - Assessment interval | | | | | |
| Active substance | gai/ha | 8 days | 8 days | 14 days | 14 days | 28 days | 28 days |
| Thiencarbazone-methyl (A2-3) | 15 g/ha | 90 | 0 | 97 | 0 | 100 | 0 |
| Thiencarbazone-methyl (A2-3) | 30 g/ha | 90 | 0 | 97 | 0 | 100 | 0 |
| (A1-13) + (A2-3) | 25 + 15 g/ha | 90 | 0 | 97 | 0 | 100 | 0 |
| (A1-13) + (A2-3) | 50 + 30 g/ha | 90 | 3 | 97 | 0 | 100 | 0 |
| Iodosulfuron-methyl-sodium (A1-16) | 7 g/ha | 90 | 0 | 97 | 0 | 100 | 0 |
| Compound (A1-87) | 15 g/ha | 90 | 0 | 97 | 0 | 99 | 0 |
| Compound (A1-41) | 30 g/ha | 90 | 14 | 98 | 10 | 100 | 0 |
| Mesosulfuron-methyl (A1-17) | 60 g/ha | 90 | 0 | 97 | 0 | 99 | 0 |
| Metsulfuron-methyl (A1-18) | 8 g/ha | 88 | 14 | 98 | 6 | 99 | 0 |
| Thifensulfuron-methyl (A1-29) | 7.5 g/ha | 90 | 0 | 98 | 0 | 100 | 0 |
| Nicosulfuron (A1-20) | 60 g/ha | 90 | 0 | 98 | 0 | 100 | 0 |
| Tribenuron-methyl (A1-31) | 30 g/ha | 91 | 10 | 98 | 1 | 100 | 0 |
| Rimsulfuron (A1-26) | 12.5 g/ha | 81 | 0 | 85 | 4 | 76 | 0 |
| Propoxycarbazone-sodium (A2-2) | 70 g/ha | 90 | 1 | 94 | 0 | 95 | 0 |
| Bispyribac-sodium (C1-1) | 50 g/ha | 90 | 23 | 98 | 30 | 99 | 0 |
| Metosulam (A3-5) | 30 g/ha | 90 | 9 | 97 | 0 | 93 | 0 |
| Imazamox (B1-2) | 40 g/ha | 90 | 0 | 97 | 0 | 99 | 0 |

According to the data disclosed in Table 2, it can clearly be demonstrated that SB574TL based sugar beet plants are fully tolerant to the application of various ALS inhibitor herbicides, i.e. tolerance has been demonstrated to representative compounds selected from all of the 3 different groups ((A), (B) and (C)), where as the conventional variety KLARINA is significantly damaged under identical growing conditions.

TABLE 3

| | | Variety characteristic | | | | | |
|---|---|---|---|---|---|---|---|
| | | BERETTA | SB574TL based sugar beet | BERETTA | SB574TL based sugar beet | BERETTA | SB574TL based sugar beet |
| | | Stage of application | | | | | |
| | | BBCH 14 | BBCH 14 | BBCH 14 | BBCH 14 | BBCH 14 | BBCH 14 |
| | | Rating | | | | | |
| | | % phyto | % phyto | % phyto | % phyto | % phyto | % phyto |
| | | Application - Assessment interval | | | | | |
| Active substance | gai/ha | 8 days | 8 days | 16 days | 16 days | 38 days | 38 days |
| Sulfosulfuron (A1-28) | 10 g/ha | 80 | 0 | 95 | 0 | 94 | 0 |
| Triasulfuron (A1-30) | 30 g/ha | 80 | 0 | 98 | 0 | 100 | 0 |
| Chlorsulfuron (A1-5) | 20 g/ha | 80 | 0 | 98 | 0 | 100 | 0 |
| Flupyrsulfuron-methyl-sodium (A1-12) | 10 g/ha | 63 | 0 | 69 | 0 | 40 | 0 |
| Prosulfuron (A1-24) | 40 g/ha | 81 | 21 | 98 | 30 | 100 | 0 |

TABLE 3-continued

| | | | | Variety characteristic | | | |
|---|---|---|---|---|---|---|---|
| | | BERETTA | SB574TL based sugar beet | BERETTA | SB574TL based sugar beet | BERETTA | SB574TL based sugar beet |
| | | | | Stage of application | | | |
| | | BBCH 14 | BBCH 14 | BBCH 14 | BBCH 14 | BBCH 14 | BBCH 14 |
| | | | | Rating | | | |
| | | % phyto | % phyto | % phyto | % phyto | % phyto | % phyto |
| | | | | Application - Assessment interval | | | |
| Active substance | gai/ha | 8 days | 8 days | 16 days | 16 days | 38 days | 38 days |
| Tritosulfuron (A1-34) | 50 g/ha | 80 | 20 | 98 | 33 | 100 | 5 |
| Flazasulfuron (A1-10) | 50 g/ha | 80 | 24 | 98 | 25 | 100 | 11 |
| Sulfometuron-methyl (A1-27) | 60 g/ha | 80 | 0 | 97 | 3 | 100 | 0 |
| Imazethapyr (B1-6) | 70 g/ha | 80 | 0 | 98 | 0 | 100 | 0 |
| Imazapyr (B1-4) | 125 g/ha | 80 | 0 | 98 | 0 | 100 | 0 |
| Imazapic (B1-3) | 70 g/ha | 80 | 14 | 98 | 0 | 100 | 0 |
| Imazaquin (B1-5) | 100 g/ha | 80 | 0 | 98 | 0 | 100 | 0 |
| Florasulam (A3-3) | 10 g/ha | 80 | 0 | 98 | 0 | 98 | 0 |
| Penoxsulam (A3-6) | 40 g/ha | 80 | 0 | 91 | 15 | 100 | 0 |
| Flumetsulam (A3-4) | 50 g/ha | 80 | 0 | 98 | 0 | 100 | 0 |
| Pyroxsulam (A3-7) | 50 g/ha | 80 | 0 | 97 | 0 | 100 | 0 |
| Flucarbazone-sodium (A2-1) | 40 g/ha | 80 | 0 | 89 | 0 | 89 | 0 |
| Trifloxisulfuron-sodium (A1-32) | 15 g/ha | 80 | 0 | 98 | 0 | 100 | 0 |

According to the data disclosed in Table 3, it can clearly be demonstrated that SB574TL based sugar beet plants are fully tolerant to the application of various ALS inhibitor herbicides, i.e. tolerance has been demonstrated to representative compounds selected from all of the 2 different groups ((A), and (B)), where as the conventional variety BERETTA is significantly damaged under identical conditions.

The invention claimed is:

1. A method for controlling unwanted vegetation in a *Beta vulgaris* growing area, the method comprising
   (a) cultivating at least one *B. vulgaris* plant comprising a mutation in a position corresponding to position 1705-1707 of an endogenous acetolactate synthase (ALS) gene of SEQ ID NO:1, thereby encoding an ALS protein containing leucine at position 569 of SEQ ID NO:2 in the *B. vulgaris* growing area, and
   (b) applying as the only ALS inhibitor herbicide(s) one or more ALS inhibitor herbicide(s) to the *B. vulgaris* growing area;
   wherein the one or more ALS herbicide(s) is selected from the group consisting of:
   amidosulfuron [CAS RN 120923-37-7] (=A1-1);
   chlorsulfuron [CAS RN 64902-72-3] (=A1-5);
   flupyrsulfuron-methyl-sodium [CAS RN 144740-54-5] (=A1-12);
   foramsulfuron [CAS RN 173159-57-4] (=A1-13);
   iodosulfuron-methyl-sodium [CAS RN 144550-36-7] (=A1-16);
   mesosulfuron-methyl [CAS RN 208465-21-8] (=A1-17);
   nicosulfuron [CAS RN 111991-09-4] (=A1-20);
   rimsulfuron [CAS RN 122931-48-0] (=A1-26);
   sulfometuron-methyl [CAS RN 74222-97-2] (=A1-27);
   sulfosulfuron [CAS RN 141776-32-1] (=A1-28);
   thifensulfuron-methyl [CAS RN 79277-27-3] (=A1-29);
   triasulfuron [CAS RN 82097-50-5] (=A1-30);
   tribenuron-methyl [CAS RN 101200-48-0] (=A1-31);
   trifloxysulfuron [CAS RN 145099-21-4] (sodium) (=A1-32);
   (A1-83) or its sodium salt (=A1-87);
   flucarbazone-sodium [CAS RN 181274-17-9] (=A2-1);
   propoxycarbazone-sodium [CAS RN 181274-15-7] (=A2-2);
   thiencarbazone-methyl [CAS RN 317815-83-1] (=A2-3);
   florasulam [CAS RN 145701-23-1] (=A3-3);
   flumetsulam [CAS RN 98967-40-9] (=A3-4);
   metosulam [CAS RN 139528-85-1] (=A3-5);
   pyroxsulam [CAS RN 422556-08-9] (=A3-7);
   imazamox [CAS RN 114311-32-9] (=B1-2);
   imazapic [CAS RN 104098-48-8] (=B1-3);
   imazapyr [CAS RN 81334-34-1] (=B1-4);
   imazaquin [CAS RN 81335-37-7] (=B1-5); and
   imazethapyr [CAS RN 81335-77-5] (=B1-6),
   wherein the *B. vulgaris* plant has a mutation in the endogenous acetolactate synthase (ALS) gene of SEQ ID NO:1, thereby encoding an ALS protein containing leucine at position 569 of SEQ ID NO:2, and wherein this mutation is the only mutation in the ALS protein that confers resistance to the one or more ALS inhibitor herbicides from step (b).

2. The method according to claim 1, wherein the one or more ALS inhibitor herbicide(s) is selected from the group consisting of:
   amidosulfuron [CAS RN 120923-37-7] (=A1-1);
   foramsulfuron [CAS RN 173159-57-4] (=A1-13);
   iodosulfuron-methyl-sodium [CAS RN 144550-36-7] (=A1-16);
   (A1-83) or its sodium salt (=A1-87);
   thiencarbazone-methyl [CAS RN 317815-83-1] (=A2-3); and
   imazamox [CAS RN 114311-32-9] (=B1-2).

3. The method according to claim 1, wherein the one or more ALS inhibitor herbicide(s) is applied in combination with at least one non-ALS inhibitor herbicide, and wherein the non-ALS inhibitor herbicide is selected from the group consisting of:
   chloridazon, clethodim, clodinafop, clodinafop-propargyl, clopyralid, cycloxydim, desmedipham, dimethenamid, dimethenamid-P, ethofumesate, fenoxaprop, fenoxaprop-P, fenoxaprop-ethyl, fenoxaprop-P-ethyl, fluazifop, fluazifop-P, fluazifop-butyl, fluazifop-P-butyl, glufosinate, glufosinate-ammonium, glufosinate-P, glufosinate-P-ammonium, glufosinate-P-sodium, glyphosate, glyphosate-isopropylammonium, haloxyfop, haloxyfop-P, haloxyfop-ethoxyethyl, haloxyfop-P-ethoxyethyl, haloxyfop-methyl, haloxyfop-P-methyl, lenacil, metamitron, phenmedipham, phenmedipham-ethyl, propaquizafop, quinmerac, quizalofop, quizalofop-ethyl, quizalofop-P, quizalofop-P-ethyl, quizalofop-P-tefuryl, and sethoxydim.

4. The method according to claim 3, wherein the non-ALS inhibitor herbicide is selected from the group consisting of:
   desmedipham, ethofumesate, glufosinate, glufosinate-ammonium, glufosinate-P, glufosinate-P-ammonium, glufosinate-P-sodium, glyphosate, glyphosate-isopropylammonium, lenacil, metamitron, phenmedipham, and phenmedipham-ethyl.

5. The method according to claim 1,
   comprising applying the one or more ALS inhibitor herbicide(s) alone or in combination with at least one herbicide that does not belong to the class of ALS inhibitor herbicides (non-ALS inhibitor herbicides),
   wherein the application of the respective herbicides
   (i) takes place jointly or simultaneously, or
   (ii) takes place at different times and/or in a plurality of portions in pre-emergence application followed by post-emergence application or early post-emergence application followed by medium or late post-emergence application.

6. The method according to claim 1, wherein the one or more ALS inhibitor herbicide(s) is a combination of foramsulfuron [CAS RN 173159-57-4] (=A1-13) and thiencarbazone-methyl [CAS RN 317815-83-1] (=A2-3), and are the only ALS inhibitor herbicides applied.

7. The method according to claim 1, wherein the one or more ALS inhibitor herbicide(s) is a combination of Compound A1-87 and iodosulfuron-methyl-sodium [CAS RN 144550-36-7] (=A1-16).

8. The method of claim 1, wherein the one or more ALS inhibitor herbicide(s) is selected from the group consisting of:

foramsulfuron [CAS RN 173159-57-4] (=A1-13), thiencarbazone-methyl [CAS RN 317815-83-1] (=A2-3), Compound A1-87 and iodosulfuron-methyl-sodium [CAS RN 144550-36-7] (=A1-16), and are the only ALS inhibitor herbicides applied.

9. The method according to claim 1, wherein the one or more ALS inhibitor herbicide(s) are the only herbicides applied.

10. The method according to claim 1, wherein the one or more ALS inhibitor herbicide(s) are the only agrochemically active compounds applied.

11. The method according to claim 1, wherein two ALS inhibitor herbicides are applied to the *B. vulgaris* growing area, and are the only ALS inhibitor herbicides applied.

12. The method according to claim 1, wherein two ALS inhibitor herbicides are applied to the *B. vulgaris* growing area, and are the only herbicides applied.

13. The method according to claim 1, wherein two ALS inhibitor herbicides are applied to the *B. vulgaris* growing area, and are the only agrochemically active compounds applied.

14. The method according to claim 1, wherein a combination of foramsulfuron [CAS RN 173159-57-4] (=A1-13) and thiencarbazone-methyl [CAS RN 317815-83-1] (=A2-3) are the only herbicides applied.

15. The method according to claim 1, wherein a combination of foramsulfuron [CAS RN 173159-57-4] (=A1-13) and thiencarbazone-methyl [CAS RN 317815-83-1] (=A2-3) are the only agrochemically active compounds applied.

16. The method according to claim 1, wherein the one or more ALS inhibitor herbicide(s) is applied at an application rate of 1 g to 200 g a.i./ha.

17. The method according to claim 1, wherein the one or more ALS inhibitor herbicide(s) is applied at an application rate of 7 g to 70 g a.i./ha.

18. The method according to claim 1, wherein the mutation was obtained in a non-transgenic way.

19. The method according to claim 1, wherein the mutation is homozygously present in the endogenous ALS gene.

* * * * *

```
                       SEQUENCE LISTING

<160> NUMBER OF SEQ ID NOS: 4

<210> SEQ ID NO 1
<211> LENGTH: 1998
<212> TYPE: DNA
<213> ORGANISM: Beta vulgaris

<400> SEQUENCE: 1
atggcggcta ccttcacaaa cccaacattt tccccttcct caactccatt aaccaaaacc      60
ctaaaatccc aatcttccat ctcttcaacc ctcccctttt ccaccccctcc caaaaccccca    120 actccactct ttcaccgtcc cctccaaatc tcatcctccc aatcccacaa atcatccgcc     180
attaaaacac aaactcaagc accttcttct ccagctattg aagattcatc tttcgtttct    240
cgatttggcc ctgatgaacc cagaaaaggg tccgatgtcc tcgttgaagc tcttgagcgt    300
gaaggtgtta ccaatgtgtt tgcttaccct ggtggtgcat ctatggaaat ccaccaagct    360
ctcacacgct ctaaaaccat ccgcaatgtc ctccctcgcc atgaacaagg cggggttttc    420
gccgccgagg gatatgctag agctactgga aaggttggtg tctgcattgc gacttctggt    480
cctggtgcta ccaacctcgt atcaggtctt gctgacgctc tccttgattc tgtccctctt    540
gttgccatca ctggccaagt tccacgccgt atgattggca ctgatgcttt tcaggagact    600
ccaattgttg aggtgacaag gtctattact aagcataatt atttagtttt ggatgtagag    660
```

```
gatattccta gaattgttaa ggaagccttt tttttagcta attctggtag gcctggacct    720
gttttgattg atcttcctaa agatattcag cagcaattgg ttgttcctga ttgggatagg    780
ccttttaagt tgggtgggta tatgtctagg ctgccaaagt ccaagttttc gacgaatgag    840
gttggacttc ttgagcagat tgtgaggttg atgagtgagt cgaagaagcc tgtcttgtat    900
gtgggaggtg ggtgtttgaa ttctagtgag gagttgagga gatttgttga gttgacaggg    960
attccggtgg ctagtacttt gatggggttg gggtcttacc cttgtaatga tgaactgtct   1020
cttcatatgt tggggatgca cgggactgtt tatgccaatt atgcggtgga taaggcggat   1080
ttgttgcttg ctttcggggt taggtttgat gatcgtgtga ccgggaagct cgaggcgttt   1140
gctagccgtg ctaagattgt gcatattgat attgactctg ctgagattgg gaagaacaag   1200
cagccccatg tgtccatttg tgctgatgtt aaattggcat tgcggggtat gaataagatt   1260
ctggagtcta gaatagggaa gctgaatttg gatttctcca gtggagaga agaattaggt   1320 gagcagaaga aggaattccc actgagtttt aagacatttg gggatgcaat tcctccacaa   1380
tatgccattc aggtgcttga tgagttgacc aatggtaatg ctattataag tactggtgtt   1440
gggcagcacc aaatgtgggc tgcgcagcat tacaagtaca gaaaccctcg ccaatggctg   1500
acctctggtg ggttggggc tatggggttt ggctaccag ccgccattgg agctgcagtt    1560
gctcgaccag atgcagtggt tgtcgatatt gatggggatg gcagttttat tatgaatgtt   1620
caagagttgg ctacaattag ggtggaaaat ctcccagtta agataatgct gctaaacaat   1680
caacatttag gtatggttgt ccaatgggaa gataggttct ataaagctaa ccgggcacat   1740
acataccttg gaaacccttc caaatctgct gatatcttcc ctgatatgct caaattcgct   1800
gaggcatgtg atattccttc tgcccgtgtt agcaacgtgg ctgatttgag gccgccatt    1860 caaacaatgt ggatactcc agggccgtac ctgctcgatg tgattgtacc gcatcaagag   1920
catgtgttgc ctatgattcc aagtggtgcc ggtttcaagg ataccattac agagggtgat   1980
ggaagaacct cttattga                                                1998
```

<210> SEQ ID NO 2
<211> LENGTH: 665
<212> TYPE: PRT
<213> ORGANISM: Beta vulgaris

<400> SEQUENCE: 2

Met Ala Ala Thr Phe Thr Asn Pro Thr Phe Ser Pro Ser Ser Thr Pro
1               5                   10                  15

Leu Thr Lys Thr Leu Lys Ser Gln Ser Ser Ile Ser Ser Thr Leu Pro
            20                  25                  30

Phe Ser Thr Pro Pro Lys Thr Pro Thr Pro Leu Phe His Arg Pro Leu
        35                  40                  45

Gln Ile Ser Ser Gln Ser His Lys Ser Ser Ala Ile Lys Thr Gln
    50                  55                  60

Thr Gln Ala Pro Ser Ser Pro Ala Ile Glu Asp Ser Ser Phe Val Ser
65                  70                  75                  80

Arg Phe Gly Pro Asp Glu Pro Lys Gly Ser Asp Val Leu Glu
            85                  90                  95

Ala Leu Glu Arg Glu Gly Val Thr Asn Val Phe Ala Tyr Pro Gly Gly
            100                 105                 110

Ala Ser Met Glu Ile His Gln Ala Leu Thr Arg Ser Lys Thr Ile Arg
        115                 120                 125

```
Asn Val Leu Pro Arg His Glu Gln Gly Gly Val Phe Ala Ala Glu Gly
    130                 135                 140
Tyr Ala Arg Ala Thr Gly Lys Val Gly Val Cys Ile Ala Thr Ser Gly
145                 150                 155                 160
Pro Gly Ala Thr Asn Leu Val Ser Gly Leu Ala Asp Ala Leu Leu Asp
                165                 170                 175
Ser Val Pro Leu Val Ala Ile Thr Gly Gln Val Pro Arg Arg Met Ile
            180                 185                 190
Gly Thr Asp Ala Phe Gln Glu Thr Pro Ile Val Glu Val Thr Arg Ser
        195                 200                 205
Ile Thr Lys His Asn Tyr Leu Val Leu Asp Val Glu Asp Ile Pro Arg
    210                 215                 220
Ile Val Lys Glu Ala Phe Phe Leu Ala Asn Ser Gly Arg Pro Gly Pro
225                 230                 235                 240
Val Leu Ile Asp Leu Pro Lys Asp Ile Gln Gln Leu Val Val Pro
                245                 250                 255
Asp Trp Asp Arg Pro Phe Lys Leu Gly Gly Tyr Met Ser Arg Leu Pro
                260                 265                 270
Lys Ser Lys Phe Ser Thr Asn Glu Val Gly Leu Leu Glu Gln Ile Val
            275                 280                 285
Arg Leu Met Ser Glu Ser Lys Lys Pro Val Leu Tyr Val Gly Gly Gly
        290                 295                 300
Cys Leu Asn Ser Ser Glu Glu Leu Arg Arg Phe Val Glu Leu Thr Gly
305                 310                 315                 320
Ile Pro Val Ala Ser Thr Leu Met Gly Leu Gly Ser Tyr Pro Cys Asn
                325                 330                 335
Asp Glu Leu Ser Leu His Met Leu Gly Met His Gly Thr Val Tyr Ala
                340                 345                 350
Asn Tyr Ala Val Asp Lys Ala Asp Leu Leu Leu Ala Phe Gly Val Arg
            355                 360                 365
Phe Asp Asp Arg Val Thr Gly Lys Leu Glu Ala Phe Ala Ser Arg Ala
        370                 375                 380
Lys Ile Val His Ile Asp Ile Asp Ser Ala Glu Ile Gly Lys Asn Lys
385                 390                 395                 400
Gln Pro His Val Ser Ile Cys Ala Asp Val Lys Leu Ala Leu Arg Gly
                405                 410                 415
Met Asn Lys Ile Leu Glu Ser Arg Ile Gly Lys Leu Asn Leu Asp Phe
                420                 425                 430
Ser Lys Trp Arg Glu Glu Leu Gly Glu Gln Lys Lys Glu Phe Pro Leu
            435                 440                 445
Ser Phe Lys Thr Phe Gly Asp Ala Ile Pro Pro Gln Tyr Ala Ile Gln
        450                 455                 460
Val Leu Asp Glu Leu Thr Asn Gly Asn Ala Ile Ile Ser Thr Gly Val
465                 470                 475                 480
Gly Gln His Gln Met Trp Ala Ala Gln His Tyr Lys Tyr Arg Asn Pro
                485                 490                 495
Arg Gln Trp Leu Thr Ser Gly Gly Leu Gly Ala Met Gly Phe Gly Leu
                500                 505                 510
Pro Ala Ala Ile Gly Ala Ala Val Ala Arg Pro Asp Ala Val Val Val
            515                 520                 525
Asp Ile Asp Gly Asp Gly Ser Phe Ile Met Asn Val Gln Glu Leu Ala
        530                 535                 540
```

| | | | | | | | | | | | | | | | |
|---|---|---|---|---|---|---|---|---|---|---|---|---|---|---|---|
|Thr|Ile|Arg|Val|Glu|Asn|Leu|Pro|Val|Lys|Ile|Met|Leu|Leu|Asn|Asn|
|545| | | | |550| | | | |555| | | | |560|

| | | | | | | | | | | | | | | | |
|---|---|---|---|---|---|---|---|---|---|---|---|---|---|---|---|
|Gln|His|Leu|Gly|Met|Val|Val|Gln|Trp|Glu|Asp|Arg|Phe|Tyr|Lys|Ala|
| | | | |565| | | | |570| | | | |575| |

| | | | | | | | | | | | | | | | |
|---|---|---|---|---|---|---|---|---|---|---|---|---|---|---|---|
|Asn|Arg|Ala|His|Thr|Tyr|Leu|Gly|Asn|Pro|Ser|Lys|Ser|Ala|Asp|Ile|
| | | | |580| | | | |585| | | | |590| |

| | | | | | | | | | | | | | | | |
|---|---|---|---|---|---|---|---|---|---|---|---|---|---|---|---|
|Phe|Pro|Asp|Met|Leu|Lys|Phe|Ala|Glu|Ala|Cys|Asp|Ile|Pro|Ser|Ala|
| | | | |595| | | | |600| | | | |605| |

| | | | | | | | | | | | | | | | |
|---|---|---|---|---|---|---|---|---|---|---|---|---|---|---|---|
|Arg|Val|Ser|Asn|Val|Ala|Asp|Leu|Arg|Ala|Ala|Ile|Gln|Thr|Met|Leu|
| | | |610| | | | |615| | | | |620| | |

| | | | | | | | | | | | | | | | |
|---|---|---|---|---|---|---|---|---|---|---|---|---|---|---|---|
|Asp|Thr|Pro|Gly|Pro|Tyr|Leu|Leu|Asp|Val|Ile|Val|Pro|His|Gln|Glu|
|625| | | | |630| | | | |635| | | | |640| |

| | | | | | | | | | | | | | | | |
|---|---|---|---|---|---|---|---|---|---|---|---|---|---|---|---|
|His|Val|Leu|Pro|Met|Ile|Pro|Ser|Gly|Ala|Gly|Phe|Lys|Asp|Thr|Ile|
| | | | |645| | | | |650| | | | |655| |

| | | | | | | | | |
|---|---|---|---|---|---|---|---|---|
|Thr|Glu|Gly|Asp|Gly|Arg|Thr|Ser|Tyr|
| | | |660| | | | |665|

<210> SEQ ID NO 3
<211> LENGTH: 1998
<212> TYPE: DNA
<213> ORGANISM: Beta vulgaris
<220> FEATURE:
<221> NAME/KEY: mutation
<222> LOCATION: (1706)..(1706)
<223> OTHER INFORMATION: Substitution of a Guanosine by a Thymidine

<400> SEQUENCE: 3

```
atggcggcta ccttcacaaa cccaacattt tccccttcct caactccatt aaccaaaacc      60
ctaaaatccc aatcttccat ctcttcaacc ctccccttt  ccaccctcc  caaaccccca    120
actccactct tcaccgtgcc cctccaaatc tcatcctccc aatccacaa  atcatccgcc    180
attaaaacac aaactcaagc accttcttct ccagctattg aagattcatc tttcgtttct    240
cgatttggcc ctgatgaacc cagaaaaggg tccgatgtcc tcgttgaagc tcttgagcgt    300
gaaggtgtta ccaatgtgtt tgcttaccct ggtggtgcat ctatggaaat ccaccaagct    360
ctcacacgct ctaaaaccat ccgcaatgtc ctccctcgcc atgaacaagg cggggttttc    420
gccgccgagg atatgctag agctactgga aaggttggtg tctgcattgc gacttctggt    480
cctggtgcta ccaacctcgt atcaggtctt gctgacgctc tccttgattc tgtccctctt    540
gttgccatca ctggccaagt tccacgccgt atgattggca ctgatgcttt tcaggagact    600
ccaattgttg aggtgacaag gtctattact aagcataatt atttagtttt ggatgtagag    660
gatattccta gaattgttaa ggaagccttt tttttagcta attctggtag gcctggacct    720
gttttgattg atcttcctaa agatattcag cagcaattgg ttgttcctga ttgggatagg    780
cctttttaagt tgggtgggta tatgtctagg ctgccaaagt ccaagttttc gacgaatgag    840
gttggacttc ttgagcagat tgtgaggttg atgagtgagt cgaagaagcc tgtcttgtat    900
gtgggaggtg ggtgtttgaa ttctagtgag agttgagga gatttgttga gttgacaggg    960
attccggtgg ctagtacttt gatggggttg gggtcttacc cttgtaatga tgaactgtct   1020
cttcatatgt tggggatgca cgggactgtt tatgccaatt atgcggtgga taaggcggat   1080
ttgttgcttg ctttcgggggt taggtttgat gatcgtgtga ccgggaagct cgaggcgttt   1140
gctagccgtg ctaagattgt gcatattgat attgactctg ctgagattgg gaagaacaag   1200
cagccccatg tgtccatttg tgctgatgtt aaattggcat tgcggggtat gaataagatt   1260
ctggagtcta gaatagggaa gctgaatttg gatttctcca agtggagaga agaattaggt   1320
```

-continued

```
gagcagaaga aggaattccc actgagtttt aagacatttg gggatgcaat tcctccacaa    1380
tatgccattc aggtgcttga tgagttgacc aatggtaatg ctattataag tactggtgtt    1440
gggcagcacc aaatgtgggc tgcgcagcat acaagtaca gaaaccctcg ccaatggctg     1500
acctctggtg ggttggggc tatggggttt gggctaccag ccgccattgg agctgcagtt     1560
gctcgaccag atgcagtggt tgtcgatatt gatggggatg cagttttat tatgaatgtt     1620 caagagttgg ctacaattag ggtggaaaat ctcccagtta agataatgct gctaaacaat    1680
caacatttag gtatggttgt ccaattggaa gataggttct ataaagctaa ccgggcacat    1740
acataccttg gaaacccttc caaatctgct gatatcttcc ctgatatgct caaattcgct    1800
gaggcatgtg atattccttc tgcccgtgtt agcaacgtgg ctgatttgag gccgccatt    1860 caaacaatgt tggatactcc agggccgtac ctgctcgatg tgattgtacc gcatcaagag    1920
catgtgttgc ctatgattcc aagtggtgcc ggtttcaagg ataccattac agagggtgat    1980
ggaagaacct cttattga                                                 1998
```

<210> SEQ ID NO 4
<211> LENGTH: 665
<212> TYPE: PRT
<213> ORGANISM: Beta vulgaris
<220> FEATURE:
<221> NAME/KEY: MISC_FEATURE
<222> LOCATION: (569)..(569)
<223> OTHER INFORMATION: Substitution of a Tryptophan by a Leucine

<400> SEQUENCE: 4

```
Met Ala Ala Thr Phe Thr Asn Pro Thr Phe Ser Pro Ser Ser Thr Pro
1               5                   10                  15

Leu Thr Lys Thr Leu Lys Ser Gln Ser Ser Ile Ser Ser Thr Leu Pro
            20                  25                  30

Phe Ser Thr Pro Pro Lys Thr Pro Thr Pro Leu Phe His Arg Pro Leu
        35                  40                  45

Gln Ile Ser Ser Ser Gln Ser His Lys Ser Ser Ala Ile Lys Thr Gln
    50                  55                  60

Thr Gln Ala Pro Ser Ser Pro Ala Ile Glu Asp Ser Ser Phe Val Ser
65                  70                  75                  80

Arg Phe Gly Pro Asp Glu Pro Arg Lys Gly Ser Asp Val Leu Val Glu
                85                  90                  95

Ala Leu Glu Arg Glu Gly Val Thr Asn Val Phe Ala Tyr Pro Gly Gly
            100                 105                 110

Ala Ser Met Glu Ile His Gln Ala Leu Thr Arg Ser Lys Thr Ile Arg
        115                 120                 125

Asn Val Leu Pro Arg His Glu Gln Gly Gly Val Phe Ala Ala Glu Gly
    130                 135                 140

Tyr Ala Arg Ala Thr Gly Lys Val Gly Val Cys Ile Ala Thr Ser Gly
145                 150                 155                 160

Pro Gly Ala Thr Asn Leu Val Ser Gly Leu Ala Asp Ala Leu Leu Asp
                165                 170                 175

Ser Val Pro Leu Val Ala Ile Thr Gly Gln Val Pro Arg Arg Met Ile
            180                 185                 190

Gly Thr Asp Ala Phe Gln Glu Thr Pro Ile Val Glu Val Thr Arg Ser
        195                 200                 205

Ile Thr Lys His Asn Tyr Leu Val Leu Asp Val Glu Asp Ile Pro Arg
    210                 215                 220
```

```
Ile Val Lys Glu Ala Phe Leu Ala Asn Ser Gly Arg Pro Gly Pro
225                 230                 235                 240

Val Leu Ile Asp Leu Pro Lys Asp Ile Gln Gln Gln Leu Val Val Pro
            245                 250                 255

Asp Trp Asp Arg Pro Phe Lys Leu Gly Gly Tyr Met Ser Arg Leu Pro
                260                 265                 270

Lys Ser Lys Phe Ser Thr Asn Glu Val Gly Leu Leu Glu Gln Ile Val
        275                 280                 285

Arg Leu Met Ser Glu Ser Lys Lys Pro Val Leu Tyr Val Gly Gly Gly
            290                 295                 300

Cys Leu Asn Ser Ser Glu Glu Leu Arg Arg Phe Val Glu Leu Thr Gly
305                 310                 315                 320

Ile Pro Val Ala Ser Thr Leu Met Gly Leu Gly Ser Tyr Pro Cys Asn
                325                 330                 335

Asp Glu Leu Ser Leu His Met Leu Gly Met His Gly Thr Val Tyr Ala
                340                 345                 350

Asn Tyr Ala Val Asp Lys Ala Asp Leu Leu Leu Ala Phe Gly Val Arg
            355                 360                 365

Phe Asp Asp Arg Val Thr Gly Lys Leu Glu Ala Phe Ala Ser Arg Ala
370                 375                 380

Lys Ile Val His Ile Asp Ile Asp Ser Ala Glu Ile Gly Lys Asn Lys
385                 390                 395                 400

Gln Pro His Val Ser Ile Cys Ala Asp Val Lys Leu Ala Leu Arg Gly
                405                 410                 415

Met Asn Lys Ile Leu Glu Ser Arg Ile Gly Lys Leu Asn Leu Asp Phe
            420                 425                 430

Ser Lys Trp Arg Glu Glu Leu Gly Glu Gln Lys Lys Glu Phe Pro Leu
        435                 440                 445

Ser Phe Lys Thr Phe Gly Asp Ala Ile Pro Pro Gln Tyr Ala Ile Gln
        450                 455                 460

Val Leu Asp Glu Leu Thr Asn Gly Asn Ala Ile Ile Ser Thr Gly Val
465                 470                 475                 480

Gly Gln His Gln Met Trp Ala Ala Gln His Tyr Lys Tyr Arg Asn Pro
                485                 490                 495

Arg Gln Trp Leu Thr Ser Gly Gly Leu Gly Ala Met Gly Phe Gly Leu
                500                 505                 510

Pro Ala Ala Ile Gly Ala Ala Val Ala Arg Pro Asp Ala Val Val Val
            515                 520                 525

Asp Ile Asp Gly Asp Gly Ser Phe Ile Met Asn Val Gln Glu Leu Ala
530                 535                 540

Thr Ile Arg Val Glu Asn Leu Pro Val Lys Ile Met Leu Leu Asn Asn
545                 550                 555                 560

Gln His Leu Gly Met Val Val Gln Leu Glu Asp Arg Phe Tyr Lys Ala
                565                 570                 575

Asn Arg Ala His Thr Tyr Leu Gly Asn Pro Ser Lys Ser Ala Asp Ile
            580                 585                 590

Phe Pro Asp Met Leu Lys Phe Ala Glu Ala Cys Asp Ile Pro Ser Ala
        595                 600                 605

Arg Val Ser Asn Val Ala Asp Leu Arg Ala Ala Ile Gln Thr Met Leu
        610                 615                 620

Asp Thr Pro Gly Pro Tyr Leu Leu Asp Val Ile Val Pro His Gln Glu
625                 630                 635                 640
```

```
His Val Leu Pro Met Ile Pro Ser Gly Ala Gly Phe Lys Asp Thr Ile
                645                 650                 655

Thr Glu Gly Asp Gly Arg Thr Ser Tyr
            660                 665
```